United States Patent
Winter et al.

(10) Patent No.: US 9,518,081 B2
(45) Date of Patent: Dec. 13, 2016

(54) PEPTIDE LIBRARIES

(75) Inventors: Gregory Paul Winter, Cambridge (GB); Christian Heinis, Bern (CH); Elise Bernard, Cambridge (GB); David Loakes, Cambridge (GB); Daniel Paul Teufel, Cambridge (GB)

(73) Assignee: BICYCLE THERAPEUTICS LIMITED, Cambridge (GB)

( * ) Notice: Subject to any disclaimer, the term of this patent is extended or adjusted under 35 U.S.C. 154(b) by 2 days.

(21) Appl. No.: 13/390,252

(22) PCT Filed: Aug. 12, 2010

(86) PCT No.: PCT/EP2010/004948
§ 371 (c)(1),
(2), (4) Date: Mar. 14, 2012

(87) PCT Pub. No.: WO2011/018227
PCT Pub. Date: Feb. 17, 2011

(65) Prior Publication Data
US 2012/0172235 A1    Jul. 5, 2012

(30) Foreign Application Priority Data
Aug. 12, 2009 (GB) .................... 0914110.2

(51) Int. Cl.
*C07K 1/04* (2006.01)
*C07K 1/00* (2006.01)
*C07K 1/113* (2006.01)
*C12N 15/10* (2006.01)

(52) U.S. Cl.
CPC ................ *C07K 1/042* (2013.01); *C07K 1/00* (2013.01); *C07K 1/113* (2013.01); *C12N 15/1037* (2013.01); *C07K 2318/00* (2013.01)

(58) Field of Classification Search
CPC ........... C07K 1/042; C07K 1/113; C07K 1/00; C07K 2318/00; C12N 15/1037
See application file for complete search history.

(56) References Cited

U.S. PATENT DOCUMENTS

2008/0311592 A1 * 12/2008 Zocchi et al. ................ 435/7.6

FOREIGN PATENT DOCUMENTS

WO    WO 9846786 A1 * 10/1998
WO    WO 2004077062 A2 * 9/2004

OTHER PUBLICATIONS

Gupta, Sayam Sem, et al., "Accelerated Bioorthogonal Conjugation: A Practical Method for the Ligation of Diverse Functional Molecules to a Polyvalent Virus Scaffold," Sep. 13, 2005, Bioconjugate Chemistry, 16, pp. 1572-1579.*
PCT International Search Report for PCT/EP2010/004948.
Heinis, et al., "Phage-encoded combinatorial chemical libraries based on bicyclic peptides", Nature Chemical Biology, 5(7):502-07 (2009).
Timmerman, et al., "Rapid and Quantitative Cyclization of Multiple Peptide Loops onto Synthetic Scaffolds for Structural Mimicry of Protein Surfaces," ChemBioChem, 6:821-24 (2005).
Notification of Reexamination for Chinese Application No. 201080035488.1, dated Aug. 12, 2016 pp. 1-12.
English translation of Notification of Reexamination for Chinese Application No. 201080035488.1, dated Sep. 7, 2016, pp. 1-11.

* cited by examiner

*Primary Examiner* — Jeremy C Flinders
(74) *Attorney, Agent, or Firm* — Convergent Law Group LLP

(57) ABSTRACT

The invention relates to a method for altering the conformational diversity of a first repertoire of polypeptide ligands, comprising a plurality of polypeptides comprising at least two reactive groups separated by a loop sequence covalently linked to a molecular scaffold which forms covalent bonds with said reactive groups, to produce a second repertoire of polypeptide ligands, comprising assembling said second repertoire from the polypeptides and structural scaffold of said first repertoire, incorporating one of the following alterations: (a) altering at least one reactive group; or (b) altering the nature of the molecular scaffold; or (c) altering the bond between at least one reactive group and the molecular scaffold; or (d) any combination of (a), (b) or (c).

11 Claims, No Drawings ns by binding to a compound which provides a structural backbone, imparting a conformation to the peptide. In particular, the invention relates to modifying the conformational diversity of libraries of such peptides by altering the interaction between the peptides and the structural backbone.

Different research teams have previously tethered polypeptides with cysteine residues to a synthetic molecular structure (Kemp, D. S. and McNamara, P. E., J. Org. Chem., 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 7 of this document shows a schematic representation of the synthesis of various loop peptide constructs. The constructs disclosed in this document rely on —SH functionalised peptides, typically comprising cysteine residues, and heteroaromatic groups on the scaffold, typically comprising benzylic halogen substituents such as bis- or tris-bromophenylbenzene. Such groups react to form a thioether linkage between the peptide and the scaffold.

In our copending unpublished international patent application PCT/GB2009/000301 we disclose the use of biological selection technology, such as phage display, to select peptides tethered to synthetic molecular structures.

SUMMARY OF THE INVENTION

The nature of the interaction between the scaffold and the polypeptide is important in determining the structural form of the peptide-scaffold conjugate. Although the prior art exploits scaffolds to impart structure to polypeptides, and therefore allows the introduction of conformational diversity through alteration of the sequence of the peptides, it does not recognise that structure as well as structural diversity can be altered by manipulating the interaction between the peptide and the scaffold, as well as changing the scaffold itself.

The present invention provides for the alteration of structure and/or the introduction of structural diversity by means of the scaffold and the scaffold-peptide interface.

In a first aspect, therefore, there is provided a method for altering the conformation of a first polypeptide ligand or group of polypeptide ligands, each polypeptide ligand comprising at least two reactive groups separated by a loop sequence covalently linked to a molecular scaffold which forms covalent bonds with said reactive groups, to produce a second polypeptide ligand or group of polypeptide ligands, comprising assembling said second ligand or group of ligands from the polypeptide(s) and scaffold of said first ligand or group of ligands, incorporating one of:

a) altering at least one reactive group; or
b) altering the nature of the molecular scaffold; or
c) altering the bond between at least one reactive group and the molecular scaffold; or
d) any combination of (a), (b) or (c).

The approaches adopted in the present invention allow the person skilled in the art to modify the conformation of any structured polypeptide comprising a polypeptide covalently linked to a molecular scaffold, as well as groups of such peptides. Altering the conformation of a structured polypeptide will affect its function. For example, where the structured polypeptide is a binding molecule, the binding specificity and/or the binding affinity may be modified. Binding affinity may be increased, or decreased. Increases in affinity can have advantages, for instance in allowing lower quantities of a therapeutic or diagnostic agent to be used. Likewise, compounds with reduced affinity may be preferred, for example to reduce background from low levels of target proteins, as T-cell receptor ligands, and the like.

Alterations in the reactive group typically comprise changes in the amino acid side chain responsible for forming the covalent bond with the scaffold. For example the reactive amine or thiol group can be substituted. This can take place by amino acid replacement, for instance the replacement of cysteine with another natural amino acid, such as lysine; replacement with an alternative amino acid, such as selenocysteine or azido phenylalanine; and modification of the environment in which the reactive group is situated in the polypeptide, for example by changing one or both of the adjacent amino acids, thus influencing the peptide structure.

Altering the nature of the molecular scaffold includes, for instance, changing the nature of the scaffold reactive group. For example, altering a tris(bromomethyl)benzene scaffold to a tris(bromomethyl)mesitylene scaffold introduce methyl groups attached to the benzene ring, and allows a lesser degree of "play" between the scaffold and the polypeptide, leading to a more rigid structure. If the structure of the polypeptide conjugate is complementary to a target, then the binding of the rigid structure to the target may be favoured over that of a more flexible structure; on the other hand if the structure of the polypeptide conjugate is not complementary, the binding of the more flexible structure to the target may be preferred, as there is more possibility for an adaptive fit between the peptide ligand and a target. A number of alternative scaffold reactive groups are available, as set forth below, and many more will be apparent to those skilled in the art.

The scaffold itself may also be altered, for instance by selecting a different molecular structure. This may have a degree of structural resemblance to the scaffold in the first repertoire, or not; thus, the invention contemplates using a structurally similar, but chemically different scaffold. Moreover, the invention comprises using a structurally different scaffold.

Altering the bond between a reactive group and the scaffold can result from alterations in the nature of a reactive group or a scaffold reactive group. Moreover, it can be a result of modification of the bond post-attachment of the scaffold. For example, oxidation of thioether linkages between the scaffold and the peptide leads to the formation of sulphoxides, which have an altered geometry and therefore impart a different structure to the polypeptide in the peptide ligand.

Alterations introduced to the scaffold, polypeptide or the bonds need not be symmetrical. For example, if there are two or three reactive groups on the peptide, only one of them need be altered to introduce increased library diversity. Alternatively, a percentage of the reactive groups can be altered; for example, 20, 30, 40 or 50% of the polypeptide molecules can be constructed with altered reactive groups in one or more positions, leaving the remaining polypeptides unmodified or modified in a different way.

Scaffold alterations, likewise, need not be symmetrical. An asymmetrical scaffold may present different scaffold reactive groups in one, two, three or more positions. Such groups may be orthogonal, dictating a particular arrangement of binding with the polypeptide, thus reducing the number of structural isomers of the peptide ligand which can be formed. Alternatively, the formation of isomers may be allowed, to promote even greater diversity.

Assembly of the libraries of the invention can itself be exploited to introduce diversity. For instance, a repertoire of polypeptides may be exposed to two or more scaffold species, and possibly a repertoire of scaffolds, leading to increased diversity through differing combinations of sequence variation and scaffold variations. If a scaffold has three scaffold reactive groups, a significant degree of variation can be introduced merely by randomising the nature of said scaffold reactive groups. Combined with the randomisation of the polypeptide sequence, this can lead to greatly increased repertoire size.

When applied to repertoires of polypeptides, the methods according to the present invention may be used to increase the structural diversity of polypeptide ligands. Moreover, further diversity can be obtained by choosing a different scaffold, which may have differing structural properties.

In a preferred embodiment, the invention comprises the generation of a group or repertoire of polypeptide ligands from smaller group of polypeptide ligands, including for example a single polypeptide ligand. In such embodiments, diversity is generated through any one or more of alteration or replacement of the scaffold, alteration of at least one reactive group in the peptide, and/or altering at least one bond between the polypeptide and the scaffold. Suitably, where necessary, the diversity of the repertoire may be further enhanced by modification of the sequence of the peptide. For example, amino acid additions, deletions or substitutions may be made between the reactive groups in the polypeptide, therefore altering the sequence of the loops subtended between the attachment points to the scaffold. For example, one loop may be altered, and a second loop may be left unchanged.

Accordingly, the invention provides a method for generating a group of diverse polypeptide ligands from a first polypeptide ligand comprising at least two reactive groups separated by a loop sequence covalently linked to a molecular scaffold which forms covalent bonds with said reactive groups, comprising assembling a group or repertoire of ligands from the polypeptide and scaffold of said first ligand or group of ligands, and incorporating one of the following alterations:

a) altering at least one reactive group; or
b) altering the nature of the molecular scaffold; or
c) altering the bond between at least one reactive group and the molecular scaffold; or
d) any combination of (a), (b) or (c); or e) modifying the sequence of the polypeptide, in combination with any one of (a) to (d).

In one embodiment, diversity may be generated by subjecting one or more loops of the polypeptide ligand to complete or partial proteolysis. Cleavage of one or more loops of the ligand can alter the structure and therefore the functional properties thereof. Advantageously, proteolysis can be used in conjunction with modification of the polypeptide sequence of one or more of the loops.

In a second aspect, the invention provides a method for increasing the conformational diversity of a first repertoire of polypeptide ligands, comprising a plurality of polypeptides comprising at least two reactive groups separated by a loop sequence covalently linked to a molecular scaffold which forms covalent bonds with said reactive groups, comprising assembling a second repertoire of peptide ligands from the polypeptides of said first repertoire and at least two structurally diverse molecular scaffold species. The structurally different molecular scaffold species may differ in molecular structure and/or the nature of one or more scaffold reactive groups.

Variation of the molecular scaffold may be used to carry out affinity maturation of selected polypeptide ligands. In one embodiment, there is provided a method for providing a polypeptide ligand comprising a polypeptide covalently linked to a molecular scaffold at two or more amino acid residues, comprising the steps of:

(a) providing a first repertoire of polypeptides;
(b) conjugating said polypeptides to a molecular scaffold which binds to the polypeptides at two or more amino acid residues, to form a first repertoire of polypeptide conjugates;
(c) screening said first repertoire for binding against a target, and selecting members of the first repertoire which bind to the target;
(d) introducing further variation into the polypeptide ligands, in accordance with the first aspect of the invention set forth above, yielding a second repertoire of polypeptide conjugates; and
(e) screening said second repertoire for improved binding to the target.

Alterations in the scaffold which increase or reduce the flexibility of the polypeptide structure, in particular, may have pronounced effects on binding affinity without necessarily altering binding specificity.

Moreover, the invention provides a method for altering the binding activity of a polypeptide ligand comprising a polypeptide comprising at least two reactive groups separated by a loop sequence covalently linked to a molecular scaffold which forms covalent bonds with said reactive groups at two or more amino acid residues, comprising the steps of:

(a) altering at least one reactive group; or
(b) altering the nature of the molecular scaffold; or
(c) altering the bond between at least one reactive group and the molecular scaffold; or
(d) any combination of (a), (b) or (c); or
(e) modifying the sequence of the polypeptide, in combination with any one of (a) to (d).

Screening may be carried out by analysis of individual molecules. Such methods are provided in WO 2004/077062 and WO 2006/078161. However, screening of individual compounds or small sets of compounds is tedious and can be expensive if large numbers of compounds are analyzed. The number of compounds that can be assayed with screening assays generally does not exceed several thousands. Since screening of large numbers of polypeptide ligands in this way can be inefficient, an improved screening capability is highly desirable.

In a preferred embodiment, the repertoires of polypeptides are provided in the form of a nucleic acid library, and incorporated as part of a genetic display system. Applicable systems include phage display, bacterial display, yeast display, ribosome or polysome display, mRNA display and in vitro expression in artificial microcapsules. The preferred technique is phage display using a filamentous bacteriophage.

The polypeptide ligand of the invention comprises at least one polypeptide loop, subtended between two reactive groups on a molecular scaffold.

Preferably, the polypeptide conjugate of the invention comprises two loops. It may specific for a single target, or multispecific, binding to two or more targets. Several such polypeptide conjugates may be incorporated together into the same molecule. For example two such polypeptide conjugates of the same specificity can be linked together via the molecular scaffold, increasing the avidity of the ligand for its targets. Alternatively, in another embodiment a plurality of polypeptide conjugates are combined to form a multimer. For example, two different polypeptide conjugates are combined to create a multispecific molecule. Alternatively, three or more polypeptide conjugates, which may be the same or different, can be combined to form multispecific ligands.

In one embodiment multivalent complexes may be constructed by linking together the molecular scaffolds, which may be the same or different.

One skilled in the art will appreciate that the choice of target molecule is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA78, Eotaxin, Eotaxin-2, Exodus-2, FGF-acidic, FGF-basic, fibroblast growth factor-10 (30). FLT3 ligand, Fractalkine (CX3C), GDNF, G-CSF, GM-CSF, GF-I, insulin, IFNy, IGF-I, IGF-II, IL-Ia, IL-1 (3, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-17a, IL-17c, IL-17d, IL-17e, IL-17f, IL-18 (IGIF), IL-21, IL-22, IL-23, IL-31, IL-32, IL-33, IL-34, Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein (30 ibid), M-CSF, MDC (67 a. a.), MDC (69 a. a.), MCP-1 (MCAF), MCP-2, MCP-3, MCP-4, MDC (67 a. a.), MDC (69 a. a.), MIG, MIP-1α, MIP-1p, MIP-3a, MIP3 (3, MIP-4, myeloid progenitor inhibitor factor-1 (MPIF-1), NAP-2, Neurturin, Nerve growth factor, P-NGF, NT-3, NT-4, Oncostatin M, PDGF-AA, PDGF-AB, PDGF-BB, PF-4, RANTES, SDFIa, SDFIp, SCF, SCGF, stem cell factor (SCF), TARC, TGF-α, TGF-β, TGF-2, TGF-3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4. Cytokine receptors include receptors for the foregoing cytokines. Chemokine targets include CC chemokine ligands CCL21/6Ckine, CCL12/MCP-5, CCL6/C10, CCL22/MDC, CCL14/HCC-1/HCC-3, CCL3L1/MIP-1 alpha Isoform LD78 beta, CCL23/Ck beta 8-1, CCL3/MIP-1 alpha, CCL28, CCL4L1/LAG-1, CCL27/CTACK, CCL4/MIP-1 beta, CCL24/Eotaxin-2/MPIF-2, CCL15/MIP-1 delta, CCL26-like/Eotaxin-3-like, CCL9/10/MIP-1 gamma, CCL26/Eotaxin-3, CCL19/MIP-3 beta, CCL11/Eotaxin, CCL20/MIP-3 alpha, CCL14a/HCC-1, CCL23/MPIF-1, CCL14b/HCC-3, CCL18/PARC, CCL16/HCC-4, CCL5/RANTES, CCL1/I-309/TCA-3, TAFA1/FAM19A1, MCK-2, TAFA5/FAM19A5, CCL2/JE/MCP-1, TAFA3/FAM19A3, CCL8/MCP-2, TAFA4/FAM19A4, CCL7/MCP-3/MARC, CCL17/TARC, CCL13/MCP-4 and CCL25/TECK; chemokine receptors include CCR1, CCR7, CCR2, CCR8, CCR3, CCR9, CCR4, CCR10, CCR5, CCRL2/LCCR/CRAM-A/B and CCR6; CXC chemokine ligands include CXCL13/BLC/BCA-1, CXCL10/IP-10/CRG-2, CXCL14/BRAK, LIX, CXCL16, CXCL15/Lungkine, CXCL5/ENA-78, CXCL9/MIG, CXCL6/GCP-2, CXCL7/NAP-2, CXCL1/2/3/GRO, CXCL4/PF4, CXCL1/GRO alpha/KC/CINC-1, CXCL12/SDF-1 alpha, CXCL2/GRO beta/MIP-2/CINC-3, CXCL12/SDF-1 beta, CXCL3/GRO gamma/CINC-2/DCIP-1, CXCL12/SDF-1, CXCL11/I-TAC, CXCL7/Thymus Chemokine-1 and CXCL8/IL-8; CXC chemokine receptors include CXCR3, CXCR7/RDC-1, CXCR4, CXCR1/IL-8 RA, CXCR5, CXCR2/IL-8 RB and CXCR6; TNF Superfamily ligands include 4-1BB Ligand/TNFSF9, LIGHT/TNFSF14, APRIL/TNFSF13, Lymphotoxin, BAFF/BLyS/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA (pan), TNF-beta/TNFSF1B, EDA-A1/Ectodysplasin A1, TRAIL/TNFSF10, EDA-A2, TRANCE/TNFSF11, Fas Ligand/TNFSF6, TWEAK/TNFSF12 and GITR Ligand/TNFSF18; TNF Superfamily receptors include 4-1BB/TNFRSF9/CD137, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNFRH3/TNFRSF26, DcTRAIL R1/TNFRSF23, TNF RI/TNFRSF1A, DcTRAIL R2/TNFRSF22, TNF RII/TNFRSF1B, DR3/TNFRSF25, TRAIL R1/TNFRSF10A, DR6/TNFRSF21, TRAIL R2/TNFRSF10B, EDAR, TRAIL R3/TNFRSF10C, Fas/TNFRSF6/CD95, TRAIL R4/TNFRSF10D, GITR/TNFRSF18, TROY/TNFRSF19, HVEM/TNFRSF14, TWEAK R/TNFRSF12, Lymphotoxin beta R/TNFRSF3 and XEDAR; Toll-Like Receptors including TLR-1, TLR-2, TLR-3, TLR-4, TLR-5, TLR-6, TLR-7, TLR-8 and TLR-9; enzymes, including Cathepsin A, Cathepsin B, Cathepsin C, Cathepsin D, Cathepsin E, Cathepsin F, MMP 1, MMP 2, MMP 3, MMP 7, MMP 8, MMP 9, MMP 10, MMP 11, MMP 12, MMP 13, MMP 14, MMP 15, MMP 16, MMP 17, MMP 19, MMP 20, MMP 21, MMP 23A, MMP 23B, MMP 26, MMP 27, MMP 28, urokinase, kallikreins, including KLK1, KLK2, KLK3, KLK4, KLK5, KLK6, KLK7, KLK8, KLK9, KLK10, KLK11, KLK12, KLK13, KLK14 and KLK15; components of the complement system; Intracellular signalling molecules and transcription factors; p53; and MDM2.

Targets may also be large plasma proteins, such as serum albumins, as set forth below.

It will be appreciated that this list is by no means exhaustive.

In a third aspect, the present invention provides a polypeptide conjugate comprising a polypeptide comprising at least three reactive groups each separated by a loop sequence, covalently linked to a molecular scaffold comprising at least three scaffold reactive groups which form covalent bonds with said reactive groups, wherein the molecular scaffold comprises at least two different scaffold reactive groups.

Preferably, the molecular scaffold comprises three different reactive groups.

Additional binding or functional activities may be attached to the N or C terminus of the peptide covalently linked to a molecular scaffold. The functional group is, for example, selected from the group consisting of: a group capable of binding to a molecule which extends the half-life of the polypeptide ligand in vivo, and a molecule which extends the half-life of the polypeptide ligand in vivo. Such a molecule can be, for instance, HSA or a cell matrix protein, and the group capable of binding to a molecule which extends the half-life of the polypeptide ligand in vivo is an antibody or antibody fragment specific for HSA or a cell matrix protein.

In one embodiment, the functional group is a binding molecule, selected from the group consisting of a second polypeptide ligand comprising a polypeptide covalently linked to a molecular scaffold, and an antibody or antibody fragment. 2, 3, 4, 5 or more polypeptide ligands may be joined together. The specificities of any two or more of these ligands may be the same or different; if they are the same, a multivalent binding structure will be formed, which has increased avidity for the target compared to univalent binding molecules. The molecular scaffolds, moreover, may be the same or different, and may subtend the same or different numbers of loops.

The functional group can moreover be an effector group, for example an antibody Fc region.

Attachments to the N or C terminus may be made prior to binding of the peptide to a molecular scaffold, or afterwards. Thus, the peptide may be produced (synthetically, or by expression of nucleic acid) with an N or C terminal polypeptide group already in place. Preferably, however, the addition to the N or C terminus takes place after the peptide has been combined with the molecular backbone to form a conjugate. For example, Fluorenylmethyloxycarbonyl chloride can be used to introduce the Fmoc protective group at the N-terminus of the polypeptide. Fmoc binds to serum albumins including HSA with high affinity, and Fmoc-Trp or FMOC-Lys bind with an increased affinity. The peptide can be synthesised with the Fmoc protecting group left on, and then coupled with the scaffold through the cysteines. An alternative is the palmitoyl moiety which also binds HSA and has, for example been used in Liraglutide to extend the half-life of this GLP-1 analogue.

The Fmoc group confers human serum albumin binding function to the bicyclic peptide. Alternatively, a conjugate of the peptide with the scaffold can be made, and then modified at the N-terminus, for example with the amine- and sulfhydryl-reactive linker N-e-maleimidocaproyloxy)succinimide ester (EMCS). Via this linker the peptide conjugate can be linked to other polypeptides, for example an antibody Fc fragment.

The binding function may be another peptide bound to a molecular scaffold, creating a multimer; another binding protein, including an antibody or antibody fragment; or any other desired entity, including serum albumin or an effector group, such as an antibody Fc region.

Additional binding or functional activities can moreover be bound directly to the molecular scaffold.

Advantageously, the molecular scaffold comprises a reactive group to which the additional activities can be bound. Preferably, this group is orthogonal with respect to the other reactive groups on the molecular scaffold to avoid interaction with the peptide. In one embodiment, the reactive group may be protected, and deprotected when necessary to conjugate the additional activities.

In another aspect, the invention further provides a kit comprising at least a peptide ligand according to the present invention.

In a still further aspect, the present invention provides a composition comprising a peptide ligand, obtainable by a method of the present invention, and a pharmaceutically acceptable carrier, diluent or excipient.

Moreover, the present invention provides a method for the treatment of disease using a peptide ligand or a composition according to the present invention.

In a further aspect, the present invention provides a method for the diagnosis, including diagnosis of disease using a peptide ligand, or a composition according to the present invention. Thus in general the binding of an analyte to a peptide ligand may be exploited to displace an agent, which leads to the generation of a signal on displacement. For example, binding of analyte (second target) can displace an enzyme (first target) bound to the peptide ligand providing the basis for a binding assay, especially if the enzyme is held to the peptide ligand through its active site.

A particular advantage of the polypeptide conjugates of the invention are smaller than binding agents of the prior art. Typically, such a ligand has a molecular weight of less than 5000 Dalton; preferably less than 4000 Dalton; and preferably less than 3000 Dalton. It will be understood that a ligand constructed by "daisy-chaining" peptide ligands as described in the second configuration of the invention will possess a higher molecular weight. Moreover, peptide ligands bound to molecules such as HSA will have a much higher molecular weight.

The small size of the ligands results from the use of small molecular scaffolds, typically 500 Dalton in mass. The peptide itself is preferably less than 27 amino acids in length, as measured between the N-terminal and C-terminal attachment points which attach it to the molecular scaffold. Further peptides may, of course, be present or be attached outside of the attachment points, lengthening the peptide structure. Each loop of the polypeptide is preferably between 0 and 9 amino acids in length, measured between adjacent attachment points. Advantageously, the loops in any peptide ligand are independently 3, 4, 5, 6, 7, 8 or 9 amino acids in length.

DETAILED DESCRIPTION OF THE INVENTION

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

A peptide ligand, as referred to herein, refers to a peptide covalently bound to a molecular scaffold. Typically, such peptides comprise two or more reactive groups which are capable of forming covalent bonds to the scaffold, and a sequence subtended between said reactive groups which is referred to as the loop sequence, since it forms a loop when the peptide is bound to the scaffold.

The reactive groups are groups capable of forming a covalent bond with the molecular scaffold. Typically, the reactive groups are present on amino acid side chains on the peptide. Preferred are amino-containing groups such as cysteine, lysine and selenocysteine.

A target is a molecule or part thereof to which the peptide ligands bind. Typically, the target will be analogous to an epitope.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Preferably, the molecular scaffold comprises at least three attachment points for the peptide, referred to as scaffold reactive groups. These groups are capable of reacting to the reactive groups on the peptide to form a covalent bond. Preferred structures for molecular scaffolds are described below.

A repertoire is a collection of variants, in this case polypeptide variants, which differ in their sequence. In some embodiments, the location and nature of the reactive groups will not vary, but the sequences forming the loops between them can be randomised. In other embodiments, the reactive groups themselves may vary. The size of a repertoire may vary, and in the present invention may depend on the purpose of the repertoire. For example, the first repertoire is advantageously a large repertoire, which may be suitable for selection using phage. Such repertoires advantageously consist of at least $10^2$, $10^3$, $10^4$, $10^5$ or more different polypeptide variants. Smaller repertoires may not be intended for selection by a genetic display system, for example phage display, and might consist of 100 diverse polypeptide variants, or fewer. For example, they may consist of 10, 20, 30 40 or 50 diverse polypeptide variants. For example, therefore, starting from a first repertoire, a subset of the members may be varied according to methods set forth herein, to produce a second, smaller repertoire which can itself be screened without using a genetic display technology such as phage display.

A group of polypeptide variants comprises at least two diverse polypeptide variants, and may comprise 5, 10, 15, 20, 25, 30, 40 50 or more diverse variants. As with smaller repertoires, groups of variants can be screened without using a genetic display technology such as phage display, but are amenable to screening using any suitable polypeptide display technology, such as solid phase polypeptide arrays, microtitre plates and the like.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, each of which has a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members.

Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

Preferably, a library of nucleic acids encodes a repertoire of polypeptides. Each nucleic acid member of the library preferably has a sequence related to one or more other members of the library. By related sequence is meant an amino acid sequence having at least 50% identity, suitably at least 60% identity, suitably at least 70% identity, suitably at least 80% identity, suitably at least 90% identity, suitably at least 95% identity, suitably at least 98% identity, suitably at least 99% identity. Identity is suitably judged across a contiguous segment of at least 10 amino acids, suitably least 12 amino acids, suitably least 14 amino acids, suitably least 16 amino acids, suitably least 17 amino acids or the full length of the reference sequence.

As used herein, altering the reactive groups or scaffolds refers to changing the chemical structure or composition of, or replacing, any one or more of the reactive groups, or any part of the scaffold. It also refers to replacing the entire scaffold.

In one embodiment, altering the reactive groups or scaffolds will result in a conformational change in the assembled peptide ligand. For instance, it includes changes which will alter bond geometries, the structure and therefore the spatial arrangement of the reactive groups on the scaffold, the structure and therefore the spatial arrangement of reactive groups on the polypeptide, the structure of the backbone itself of the scaffold, and combinations of such features. Also included are changes which affect the flexibility of bonds and linkages, which can alter the level of adaptive fit which can be expected of a peptide ligand.

Conformational diversity, as referred to herein, is the degree of different conformational options for a peptide ligand in a repertoire of peptide ligands. If a repertoire of ligands is constructed with one scaffold, the diversity will result from variations in the peptide sequence. In accordance with the present invention, further diversity can be achieved by varying the way in which the peptide attaches to the scaffold, or the scaffold itself. In the context of a repertoire, variation can include a number of options for any given change, thus introducing still further diversity. The resulting repertoires thus cover a diversity space not covered by the original repertoire. This space may be larger, smaller or partly overlapping.

Increasing Ligand Diversity

In general, peptide ligand repertoires may be prepared by techniques known in the prior art, or described herein. The basic components of the ligands, especially the molecular scaffold and the polypeptide components, are known from Timmerman et al., 2005 ChemBioChem 6:821-824, as well as WO2004/077062, WO2006/078161 and WO2008/013454. The use of phage display to select polypeptides complexed with molecular scaffolds is described in Heinis et al., 2009, Nature Chemical Biology, 5:502-507, as well as our copending unpublished international patent application PCT/GB09/000301. Each of these documents is incorporated herein by reference. Preferred methods for constructing ligands and ligand repertoires according to the invention, and the use of phage display, are described in more detail below.

In general, modification of the scaffold-peptide interface can be exploited to increase repertoire diversity, or to reduce it if desired. As set forth above, there are three fundamental routes to achieving this aim: (a) altering the reactive groups of the polypeptide; (b) altering the scaffold, including the reactive groups of the scaffold; (c) altering the bond between the polypeptide and the scaffold, especially after the bond has been formed. Combinations of more than one method are also possible.

(A) Construction Ligand Repertoires (i) Molecular Scaffold

The molecular scaffold is sometimes referred to as the 'molecular core' or 'connector compound'. This molecule, which is in some embodiments an aromatic small molecule, comprises scaffold reactive groups which are capable of forming covalent bonds with a peptide. Reactive groups on the peptide interact with the scaffold reactive groups to form said covalent bonds.

Suitably the molecular scaffold may be, or may be based on, natural monomers such as nucleosides, sugars, or steroids. Suitably the molecular scaffold may comprise a short polymer of such entities, such as a dimer or a trimer.

A very wide variety of scaffold structures is known, and has been catalogued in the art, for instance in the CAS registry. See Lipkus et al., (2008) J Org Chem 73:4443-4451. Factors which contribute to diversity of structure are also known, such as the size and position of heteroatoms.

Suitably the molecular scaffold is a compound of known toxicity, suitably of low toxicity. Examples of suitable compounds include cholesterols, nucleotides, steroids, or existing drugs such as tamazepam.

Suitably the molecular scaffold may be a macromolecule. Suitably the molecular scaffold is a macromolecule composed of amino acids, nucleotides or carbohydrates.

Suitably the molecular scaffold comprises reactive groups that are capable of reacting with functional group(s) of the target polypeptide to form covalent bonds.

The molecular scaffold of the invention contains chemical groups that allow functional groups of the polypeptide of the encoded library of the invention to form covalent links with the molecular scaffold. Said chemical groups are selected from a wide range of functionalities including benzylic halides, α-halocarboxylic acids or amides, acryloyl moieties, amines, thiols, alcohols, ketones, aldehydes, nitriles, carboxylic acids, esters, alkenes, alkynes, anhydrides, succinimides, maleimides, azides, alkyl halides and acyl halides.

Suitably the molecular scaffold may comprise or may consist of tris(bromomethyl)benzene, especially 1,3,5-Tris(bromomethyl)benzene ('TBMB'), or a derivative thereof.

In some embodiments the molecular scaffold may have a tetrahedral geometry such that reaction of four functional groups of the encoded polypeptide with the molecular scaffold generates not more than two product isomers. Other geometries are also possible; indeed, an almost infinite number of scaffold geometries is possible, leading to greater possibilities for peptide ligand diversification.

A suitable molecular scaffold is 2,4,6-Tris(bromomethyl) mesitylene. It is similar to 1,3,5-Tris(bromomethyl)benzene but contains additionally three methyl groups attached to the benzene ring. In the case of this scaffold, the additional methyl groups may form further contacts with the polypeptide and hence add additional structural constraint. Thus, a different diversity range is achieved than with 1,3,5-Tris(bromomethyl)benzene.

Of course, the methyl groups need not be added at every position; and the positions of the substitutions need not be symmetrical. Even further diversity can, therefore, be achieved.

The molecular scaffold of the present invention is selected from either a small molecule or a macromolecular structure. The said molecular scaffold is composed of organic, inorganic or organic and inorganic components.

In a preferred embodiment, the molecular scaffold is a small organic molecule as for example a linear alkane. More suitably the molecular scaffold is a branched alkane, a cyclic alkane, a polycyclic alkane, an aromate, a heterocyclic alkane or a heterocyclic aromate, which offer the advantage of being less flexible (i.e. more rigid). Most suitably the molecular scaffold comprises at least one benzylic group.

In another embodiment, the molecular scaffold is selected from a macromolecular structure as for example a polypeptide, a polynucleotide or a polysaccharide.

(ii) Polypeptide

As set forth in more detail below, the polypeptide element of the peptide ligand comprises two or more reactive groups, preferably three or more reactive groups, which are responsible for binding to the scaffold; and loop sequences between the reactive groups. Diversity can be obtained, as in the prior art, by varying the sequence of the loops. The reactive group for conjugating the peptide to the molecular scaffold is, in one embodiment, a functionalised —SH group. A preferred amino acid having such a group is cysteine. However, other reactive groups may be used in conjunction with or instead of cysteine in any given polypeptide. For example, the two reactive groups may comprise one cysteine and one further suitable reactive group, which might for example comprise methionine, lysine, selenocysteine or other(s). In accordance with the present invention, further diversification can be achieved by variation of the reactive groups.

The reactive groups of the polypeptides are suitably provided by side chains of natural or non-natural amino acids. The reactive groups of the encoded polypeptides are suitably selected from thiol groups, amino groups, carboxyl groups, guanidinyl groups, phenolic groups or hydroxyl groups. The reactive groups of the encoded polypeptides may suitably be selected from azide, keto-carbonyl, alkyne, vinyl, or aryl halide groups. The reactive groups of the encoded polypeptides for linking to a molecular scaffold may suitably be the amino or carboxy termini of the polypeptide.

In some embodiments each of the reactive groups of the polypeptide for linking to a molecular scaffold are of the same type. For example, each reactive group may be a cysteine residue.

In some embodiments the reactive groups for linking to a molecular scaffold may comprise two or more different types, or may comprise three or more different types. For example, the reactive groups may comprise two cysteine residues and one methionine or lysine residue, or may comprise one cysteine residue, one methionine or lysine residue and one N-terminal amine, or any group selected from the list set forth above.

Cysteine is useful in the context of peptide ligands because it has the advantage that its reactivity is most different from all other amino acids. Scaffold reactive groups that could be used on the molecular scaffold to react with thiol groups of cysteines are benzylic halides, .α-halocarboxylic acids or amides, acryloyl moieties, aziridines, vinylsulfones, Examples are bromomethylbenzene (the scaffold reactive group exemplified by TBMB). Other scaffold reactive groups that are used to couple selectively compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Any variation and combination of different scaffold reactive groups is also possible.

Selenocysteine is a natural amino acid which has a similar reactivity to cysteine and can be used for the same reactions. Thus, wherever cysteine is mentioned, it is typically acceptable to substitute selenocysteine unless the context suggests otherwise.

Lysines (and primary amines of the N-terminus of peptides) are also suited as reactive groups to modify peptides on phage by linking to a molecular scaffold. However, in the event that phage is used for selection, lysines are more abundant in phage proteins than cysteines and there is a higher risk that phage particles might become cross-linked or that they might lose their infectivity. Nevertheless, it has been found that lysines are especially useful in intramolecular reactions (e.g. when a molecular scaffold is already linked to the phage peptide) to form a second or consecutive linkage with the molecular scaffold. In this case the molecular scaffold may react preferentially with lysines of the displayed peptide (in particular lysines that are in close proximity). Scaffold reactive groups that react selectively with primary amines are activated esters such as succinimides, aldehydes or alkyl halides.

In the bromomethyl group that is used in a number of the accompanying examples, the electrons of the benzene ring can stabilize the cationic transition state. This particular alkyl halide is therefore 100-1000 times more reactive than alkyl halides that are not connected to a benzene (more generally, an (heterocyclic) aromatic system) group.

Examples of succinimides for use as molecular scaffold include tris-(succinimidyl aminotriacetate), 1,3,5-Benzenetriacetic acid. Examples of aldehydes for use as molecular scaffold include Triformylmethane, and benzene 1,3,5 tris-carbaldehyde (1,3,5-Trisformylbenzene). Examples of alkyl halides for use as molecular scaffold include 1,3,5-Tris(bromomethyl)-2,4,6-trimethylbenzene, 1,3,5-Tris(bromomethyl)benzene, 1,3,5-Tris(bromomethyl)-2,4,6-triethylbenzene.

In some embodiments, molecular linkers or modifications may be added to (or to create) reactive groups of the encoded polypeptides before attachment of the molecular scaffold wherein said linkers or modifications are capable to react with the molecular scaffold.

The amino acids with reactive groups for linking to a molecular scaffold may be located at any suitable positions within the encoded polypeptide. In order to influence the particular structures or loops created, the positions of the amino acids having the reactive groups may be varied by the skilled operator, e.g. by manipulation of the nucleic acid encoding the polypeptide in order to mutate the polypeptide produced.

Each of the amino acids of the encoded polypeptide may be a target for mutagenesis (e.g. restricted variance mutagenesis) according to the needs of the skilled worker or the purpose to which the invention is being applied. Clearly at least two reactive groups for bonding to the molecular scaffold are required on the polypeptide of interest. Amino acids other than those required for bonding to the molecular scaffold may be freely varied according to operator needs and are termed 'variable amino acids'. Said variable amino acids of the encoded polypeptide (e.g. polypeptide library member(s)) may be randomised, partially randomised, or constant.

The polypeptide comprises a molecular scaffold binding segment. This is the region to which the molecular scaffold is attached. Suitably the commentary regarding reactive groups on the polypeptide is applied to this binding segment. Suitably the molecular scaffold binding segment of the target polypeptide comprises 1 to 27 amino acid residues, suitably 5 to 20 amino acid residues. Suitably the molecular scaffold binding segment of the target polypeptide comprises fewer than 10 amino acids. This has the advantage of imposing further conformational constraint onto the polypeptide segment when it is attached to the molecular scaffold.

The target polypeptide suitably comprises the sequence $XC(X)_6C(X)_6CX$, wherein X stands for a random natural amino acid. Suitably, in the formulae mentioned herein, C may be replaced with another amino acid which forms a covalent linkage with a scaffold reactive group.

The target polypeptide suitably comprises the sequence $(X)_l Y(X)_m Y(X)_n Y(X)_o$, wherein Y represents an amino acid with a reactive group, X represents a random amino acid, m and n are numbers between 1 and 20 defining the length of intervening polypeptide segments and l and o are numbers between 0 and 20 defining the length of the flanking polypeptide segments.

In some embodiments, the peptide ligand of the invention may comprise a polypeptide with the sequence $C(X)_6 C(X)_6 C$. In one embodiment, a library member or peptide ligand of the invention may comprise a mesitylene molecular scaffold and a polypeptide with the sequence $C(X)_6 C(X)_6 C$, wherein the polypeptide is tethered to the exocyclic methyl groups of the molecular scaffold via the cysteine residues of the polypeptide forming three thioether bonds therewith, and wherein X stands for an amino acid, (suitably a natural amino acid).

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the encoded polypeptide of the invention are reacted with molecular linkers wherein said linkers are capable to react with a molecular scaffold so that the linker will intervene between the molecular scaffold and the polypeptide in the final bonded state.

Suitable amino acids of the members of the genetically encoded combinatorial chemical libraries can be replaced by any natural or non-natural amino acid. Excluded from these exchangeable amino acids are the ones harbouring functional groups for cross-linking the polypeptides to a molecular core. A group of adjacent amino acids that can be varied is defined as a polypeptide segment. The size of a single polypeptide segment suitably ranges from 1 to 20 amino acids. The polypeptide segments have either random sequences, constant sequences or sequences with random and constant amino acids. The amino acids with reactive groups are either located in defined or random positions within the encoded polypeptide of the invention.

In one embodiment, the polypeptide segments that are bounded by two amino acids harbouring reactive groups for bonding with a molecular scaffold/molecular core are short amino acid sequences of 10 or fewer amino acids. Reaction of said encoded polypeptide sequences with a molecular core generates library members with high conformational constraint. Conformational constrained ligands are generally more specific and have higher binding affinities. The conformational constraint can also protect the ligands from proteolytic degradation for example in bodily fluids.

In one embodiment, an encoded polypeptide with three reactive groups has the sequence $(X)_lY(X)_mY(X)_nY(X)_o$, wherein Y represents an amino acid with a reactive group, X represents a random amino acid, m and n are numbers between 1 and 20 defining the length of intervening polypeptide segments and l and o are numbers between 0 and 20 defining the length of the flanking polypeptide segments.

In a preferred embodiment, an encoded polypeptide library of the invention has the sequence $AC(X)_6C(X)_6CG$ (SEQ ID No. 1), wherein A represents alanine, C represents cysteine, X represents a random natural amino acid and G represents glycine.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase.

The unnatural amino acids incorporated into peptides and proteins on phage may include 1) a ketone reactive group (as found in para or meta acetyl-phenylalanine) that can be specifically reacted with hydrazines, hydroxylamines and their derivatives (Addition of the keto reactive group to the genetic code of *Escherichia coli*. Wang L, Zhang Z, Brock A, Schultz P G. Proc Natl Acad Sci USA. 2003 Jan. 7; 100(1):56-61; Bioorg Med Chem Lett. 2006 Oct. 15; 16(20): 5356-9. Genetic introduction of a diketone-containing amino acid into proteins. Zeng H, Xie J, Schultz P G), 2) azides (as found in p-azido-phenylalanine) that can be reacted with alkynes via copper catalysed "click chemistry" or strain promoted (3+2) cyloadditions to form the corresponding triazoles (Addition of p-azido-L-phenylalanine to the genetic code of *Escherichia coli*. Chin J W, Santoro S W, Martin A B, King D S, Wang L, Schultz P G. J Am Chem Soc. 2002 Aug. 7; 124(31):9026-7; Adding amino acids with novel reactivity to the genetic code of *Saccharomyces cerevisiae*. Deiters A, Cropp T A, Mukherji M, Chin J W, Anderson J C, Schultz P G. J Am Chem Soc. 2003 Oct. 1; 125(39):11782-3), or azides that can be reacted with aryl phosphines, via a Staudinger ligation (Selective Staudinger modification of proteins containing p-azidophenylalanine. Tsao M L, Tian F, Schultz P G. Chembiochem. 2005 December; 6(12):2147-9), to form the corresponding amides, 4) Alkynes that can be reacted with azides to form the corresponding triazole (In vivo incorporation of an alkyne into proteins in *Escherichia coli*. Deiters A, Schultz P G. Bioorg Med Chem Lett. 2005 Mar. 1; 15(5):1521-4), 5) Boronic acids (boronates) than can be specifically reacted with compounds containing more than one appropriately spaced hydroxyl group or undergo palladium mediated coupling with halogenated compounds (Angew Chem Int Ed Engl. 2008; 47(43):8220-3. A genetically encoded boronate-containing amino acid, Brustad E, Bushey M L, Lee J W, Groff D, Liu W, Schultz P G), 6) Metal chelating amino acids, including those bearing bipyridyls, that can specifically co-ordinate a metal ion (Angew Chem Int Ed Engl. 2007; 46(48):9239-42. A genetically encoded bidentate, metal-binding amino acid. Xie J, Liu W, Schultz P G).

Unnatural amino acids may be incorporated into proteins and peptides displayed on phage by transforming *E. coli* with plasmids or combinations of plasmids bearing: 1) the orthogonal aminoacyl-tRNA synthetase and tRNA that direct the incorporation of the unnatural amino acid in response to a codon, 2) The phage DNA or phagemid plasmid altered to contain the selected codon at the site of unnatural amino acid incorporation (Proc Natl Acad Sci USA. 2008 Nov. 18; 105(46):17688-93. Protein evolution with an expanded genetic code. Liu C C, Mack A V, Tsao M L, Mills J H, Lee H S, Choe H, Farzan M, Schultz P G, Smider W; A phage display system with unnatural amino acids. Tian F, Tsao M L, Schultz P G. J Am Chem Soc. 2004 Dec. 15; 126(49):15962-3). The orthogonal aminoacyl-tRNA synthetase and tRNA may be derived from the *Methancoccus janaschii* tyrosyl pair or a synthetase (Addition of a photocrosslinking amino acid to the genetic code of *Escherichia coli*. Chin J W, Martin A B, King D S, Wang L, Schultz P G. Proc Natl Acad Sci USA. 2002 Aug. 20; 99(17):11020-4) and tRNA pair that naturally incorporates pyrrolysine (Multistep engineering of pyrrolysyl-tRNA synthetase to genetically encode N(epsilon)-(o-azidobenzyloxycarbonyl) lysine for site-specific protein modification. Yanagisawa T, Ishii R, Fukunaga R, Kobayashi T, Sakamoto K, Yokoyama S. Chem Biol. 2008 Nov. 24; 15(11):1187-97; Genetically encoding N(epsilon)-acetyllysine in recombinant proteins. Neumann H, Peak-Chew S Y, Chin J W. Nat Chem Biol. 2008 April; 4(4):232-4. Epub 2008 Feb. 17). The codon for incorporation may be the amber codon (UAG) another stop codon (UGA, or UAA), alternatively it may be a four base codon. The aminoacyl-tRNA synthetase and tRNA may be produced from existing vectors, including the pBK series of vectors, pSUP (Efficient incorporation of unnatural amino acids into proteins in *Escherichia coli*. Ryu Y, Schultz P G. Nat Methods. 2006 April; 3(4):263-5) vectors and pDULE vectors (Nat Methods. 2005 May; 2(5):377-84. Photo-cross-linking interacting proteins with a genetically encoded benzophenone. Farrell I S, Toroney R, Hazen J L, Mehl R A, Chin J W). The *E. coli* strain used will express the F' pilus (generally via a tra operon). When amber suppression is used the *E. coli* strain will not itself contain an active amber suppressor tRNA gene. The amino acid will be added to the growth media, preferably at a final concentration of 1 mM or greater. Efficiency of amino acid incorporation may be enhanced by using an expression construct with an orthogonal ribosome binding site and translating the gene with ribo-X (Evolved orthogonal ribosomes enhance the efficiency of synthetic genetic code expansion. Wang K, Neumann H, Peak-Chew S Y, Chin J W. Nat Biotechnol. 2007 July; 25(7):770-7). This may allow efficient multi-site incorporation of the unnatural amino acid providing multiple sites of attachment to the ligand.

(iv) Post Attachment Modification

In some embodiments the polypeptide-molecular scaffold complex may be modified at a time following attachment.

Protease Cleavage

In some embodiments, the polypeptide elements of the invention are proteolytically cleaved once they are tethered to a molecular scaffold/molecular core. The cleavage generates ligands having discrete peptide fragments tethered to a molecular scaffold/molecular core.

For example, one or more amide bonds of the polypeptide may be proteolytically cleaved after tethering the polypeptide to the molecular core. This has the advantage of creating short polypeptides, each joined to the molecular scaffold by at least one covalent bond, but which present different molecular structures which are retained in a complex comprising the nucleic acid encoding the parent polypeptide. The polypeptide cleavage is suitably catalysed by any suitable means known in the art such as controlled hydrolysis or more suitably enzymatic cleavage by a suitable protease. The protease may be any suitable protease but is preferably a protease with a specific polypeptide recognition sequence or motif. This advantageously leads to production of more defined and/or more predictable polypeptide cleavage products. Indeed, in this embodiment, protease recognition sequences may be systematically added or removed from the target polypeptide, for example by manipulation of the nucleic acid(s) encoding it. This advantageously provides a greater degree of control and permits greater diversity to be produced in the molecules displayed according to the present invention. Thus, enhanced diversity may be obtained by varying the nature and position of protease cleavage sites in a polypeptide molecule. Most suitably the polypeptide comprises at least one protease recognition site. Suitably each said cleavage site is comprised within amino acid sequence(s) in between reactive groups on the polypeptide used for covalent bonding to the molecular scaffold. Suitably each said recognition site is comprised within amino acid sequence(s) in between reactive groups on the polypeptide used for covalent bonding to the molecular scaffold.

The peptide loops are suitably cleaved with a protease that recognizes and processes polypeptides at specific amino acid positions such as trypsin (arginine or lysine in P1 position) or thermolysin (aliphatic side chains in P1 position). The enzyme is used at a concentration that allows efficient processing of the peptide loops of the displayed molecule but spares the phage particle. The optimal conditions can vary depending on the length of the polypeptide loops and on the protease used. Trypsin for example is typically used at 200 nM in TBS-Ca buffer (25 mM Tris HCl/137 mM NaCl/1 mM $CaCl_2$, pH 7.4) for 10 min at 10° C. A whole range of proteases that are suitable to modify displayed polypeptides but that spare the phage are described in Kristensen, P. and Winter, G. (Proteolytic selection for protein folding using filamentous bacteriophages; Fold Des. 1998; 3(5):321-8). The enzymatic processing of peptide on phage may be a 'partial proteolysis' since it cannot be excluded that a limited number of phage coat proteins are cleaved. Thus in optimisation of the conditions, the best balance between maximised cleavage of the target and maximum sparing of the phage particles is suitably chosen.

Suitably the target polypeptide comprises at least one such proteolytic cleavage site. Suitably the target polypeptide comprises at least two such proteolytic cleavage sites. Suitably the target polypeptide comprises at least three such proteolytic cleavage sites.

In each such proteolysis embodiment, suitably the said protease site(s) are located within the target polypeptide loops subtended by the molecular scaffold. This has the advantage that the molecular scaffold is retained on the complex, as otherwise the polypeptide-molecular scaffold complex may be separated from the nucleic acid encoding the target polypeptide, which is undesirable for the majority of applications of the invention.

The use of short loops (short being e.g. 6 amino acid residues or less) may compromise the ability of some proteases to cleave within the loops. In this case it may be desirable to select longer loops which are likely to be more accessible to the protease. Furthermore after cleavage of the loops by endoprotease, it may be desirable to cut back the loops further with other endoproteases, or indeed by exoproteases, such as carboxypeptidases or aminopeptidases.

When the target polypeptide comprises more than one such protease site, suitably each of the sites occurs between two covalent bonds made between the target polypeptide and the molecular scaffold. Multiple cleavage sites may occur between bonds if necessary.

In cleavage embodiments, suitably the parent polypeptide will be considered as a whole for the assessment of whether or not it is attached to the molecular scaffold by at least two or three covalent bonds. More suitably the target polypeptide will be considered to be the intact (uncleaved) polypeptide when assessing whether or not it is attached to the molecular scaffold by at least three covalent bonds.

Protease Resistance

In another embodiment, the polypeptides may be resistant to protease cleavage. In general, tightly folded polypeptide structures are more resistant to proteases, since the protease cannot physically access the polypeptide to cleave it. Therefore, manipulation of the scaffold and scaffold attachment in the peptide ligand can modulate protease sensitivity, by influencing the folding of the polypeptide loop.

As indicated in the preceding section, a protease step can be introduced to cleave accessible sites within loops attached to a chemical scaffold. If a repertoire of peptide conjugates is displayed on phage, this leads to peptides each joined to the chemical scaffold by at least one covalent bond, but retained in a complex comprising the nucleic acid encoding the parent polypeptide. The treatment of the chemically modified phage with protease before selection with antigen is expected to give rise to phage bearing peptide conjugates with cleaved loop(s), and also to phage bearing peptide conjugates with uncleaved loop(s) due to lack of a cleavage site, or otherwise being resistant to cleavage. It is possible to distinguish these species if one binds to antigen and the other does not, by comparing the binding of the selected phage clones to target antigen before and after protease treatment. Thus the species with cleaved loops will be expected to bind after protease treatment, but not before; whereas the protease-resistant species will be expected to bind both before and after treatment. Note that if a conjugate binds with both cleaved and uncleaved loops (as with PK15 after kallikrein cleavage; see Heinis et al, 2009), it may be incorrectly identified as protease resistant. This shows the importance of using a direct method for checking cleavage, for example by synthesizing the peptide conjugates chemically, and checking for evidence of cleavage, for example by mass spectrometry.

If cleaved loop conjugates are preferred to protease resistant conjugates, it will be advantageous to treat the chemically modified phage repertoire with protease before the first round of selection, and to continue to use the same protease, or one with a common cut-site, in subsequent rounds. However protease resistant conjugates may alternatively be desired. Such peptides may be useful for oral administration to survive the gut proteases, or those otherwise subject to proteolytic attack in the blood, tissues or cells. In this case, a first round of selection without protease, followed by a subsequent round of selection with protease, should favour the selection of the resistant species.

The use of protease has further utility during the selection process. For example, some unformed loops (linear segments of sequence) may be present in the libraries because (a) errors in the synthesis of the nucleotides have failed to encode a required cysteine residue, or (b) a required cysteine residue has made a disulphide bond to free cysteine in solution (perhaps due to inadequate reduction or re-oxidation), or has reacted in an irreversible manner (for example is oxidized to cysteic acid, or one of the required cysteines has reacted with a different molecule of the scaffold to the others). As linear segments of sequence are more susceptible to protease attack than loops, then, subject to a cleavage site being present, it may be possible to avoid such binders using protease.

A protease step (in the presence of reducing agent) is also advantageous to eliminate loops that have formed via disulphides between the required cysteines rather than through the chemical scaffold. This may be expected if there is inadequate reduction (or subsequent reoxidation) of the cysteines on the phages. For this reason we used degassed buffers during the chemical cross-linking step; we also kept low levels of the reducing agent (TCEP) during the reaction with TBMB to maintain the reducing environment. Nevertheless, after the first round of selection, we found many sequences that included four cysteine residues (the three required cysteine residues, and a further cysteine residue in the loop), for example CFNSEWSCLQSCSNC (SEQ ID No. 2) in the selections of repertoires against MDM2 (see Example 1). Such extra cysteines are expected to be present in the peptide repertoires, as the synthetic nucleotide library includes random codons (NNK diversity: where N represents a 25% mix each of adenine, thymine, guanine, and cytosine nucleotides, and K represents a 50% mix each of thymine and guanine nucleotides). Under some conditions, for example if there is inadequate reduction, or incomplete reaction of the required cysteines with the chemical scaffold (perhaps due to competing reactions for the scaffold by amino groups or water), an extra cysteine may be expected, under oxidising conditions, to form disulphide loops with one of the three required cysteines. Alternatively an extra cysteine may react with the scaffold, leaving two of the required cysteines to form disulphide-closed loops.

Whatever the exact mechanism behind their generation, such disulphide-closed loops may compete with the scaffold-closed loops, and predominate. It should be possible to reduce the frequency of the extra cysteines by using synthetic nucleotide libraries built from triplets, rather than monomers, so avoiding cysteine codons in the loops; and/or to undertake the selections in the presence of reducing agent, so as to open the disulphide-closed loops. More conveniently we have found that the treatment of the chemically modified phage repertoires with protease in the presence of reducing agent (such as dithiothreitol), so as to open and then cleave the loops, helps to minimise the contribution of such species.

In a preferred embodiment, therefore, the polypeptide ligands of the invention are substantially protease resistant. The invention therefore provides a method for selecting a peptide ligand having increased protease resistance, comprising the steps of:
(a) providing a first repertoire of polypeptides;
(b) conjugating said polypeptides to a molecular scaffold which binds to the polypeptides at two or more amino acid residues, to form a repertoire of polypeptide conjugates;
(c) screening said repertoire for binding against a target, and selecting members of the first repertoire which bind to the target;
(d) optionally treating the selected repertoire with reducing agent
(d) subjecting the repertoire to selection for protease resistance; and
(e) further screening said repertoire for binding to the target.

In the most preferred embodiment, the protease step is included before the screening of repertoire. The invention accordingly provides a method of selecting a peptide ligand having increased protease resistance, comprising the steps of:
(a) providing a first repertoire of polypeptides;
(b) conjugating said polypeptides to a molecular scaffold which binds to the polypeptides at two or more amino acid residues, to form a repertoire of polypeptide conjugates;
(c) optionally treating the repertoire with reducing agent
(d) subjecting the repertoire to selection for protease resistance; and
(e) screening said repertoire for binding against a target, and selecting members of the first repertoire which bind to the target.

A screen for protease resistance can simply take the form of limited digestion with a protease; those members of the repertoire which are sensitive to proteases will be eliminated. Most desirable will be to use a protease that is active under the conditions in which the bicyclic peptide will be used, for example in the presence of serum.

Bond Modification

Bonds in the scaffold, or between the scaffold and the polypeptide, may be modified post-attachment to change the structure of the peptide ligand. For example, thioether bonds may oxidized to sulphones, which alters the stereochemistry of the bond and therefore the structure of the peptide loop(s) subtended at the scaffold attachment point.

More generally, groups containing heteroatoms may be oxidized or reduced to alter bond stereochemistry, thus introducing further levels of diversity into the peptide ligand.

(v) Synthesis

It should be noted that once the polypeptide of interest is isolated or identified according to the present invention, then its subsequent synthesis may be simplified wherever possible. For example, the sequence of the polypeptide of interest may be determined, and it may be manufactured synthetically by standard techniques followed by reaction with a molecular scaffold in vitro. When this is performed, standard chemistry may be used since there is no longer any need to preserve the functionality or integrity of the genetically encoded carrier particle. This enables the rapid large scale preparation of soluble material for further downstream experiments or validation. In this regard, large scale preparation of the candidates or leads identified by the methods of the present invention could be accomplished using conventional chemistry such as that disclosed in Timmerman et al.

Thus, the invention also relates to manufacture of polypeptides or conjugates selected as set out herein, wherein the manufacture comprises optional further steps as explained below. Most suitably these steps are carried out on the end product polypeptide/conjugate made by chemical synthesis, rather than on the phage.

Optionally amino acid residues in the polypeptide of interest may be substituted when manufacturing a conjugate or complex e.g. after the initial isolation/identification step.

Peptides can also be extended, to incorporate for example another loop and therefore introduce multiple specificities.

To extend the peptide, it may simply be extended chemically at its N-terminus or C-terminus using standard solid phase or solution phase chemistry. Standard activation/bioconjugation chemistry may be used to introduce an activatable N- or C-terminus. Alternatively additions may be made by fragment condensation or native chemical ligation e.g. as described in (Dawson P E, Muir T W, Clark-Lewis I, Kent, S B H. 1994. Synthesis of Proteins by Native Chemical Ligation. Science 266:776-779), or by enzymes, for example using subtiligase as described in (Subtiligase: a tool for semisynthesis of proteins Chang T K, Jackson D Y, Burnier J P, Wells J A Proc Natl Acad Sci USA. 1994 Dec. 20; 91(26):12544-8 or in Bioorganic & Medicinal Chemistry Letters Tags for labelling protein N-termini with subtiligase for proteomics Volume 18, Issue 22, 15 Nov. 2008, Pages 6000-6003 Tags for labeling protein N-termini with subtiligase for proteomics Hikari A. I. Yoshihara, Sami Mahrus and James A. Wells).

Alternatively, the peptides may be extended or modified by further conjugation through disulphide bonds. This has the additional advantage of allowing first and second peptide to dissociate from each other once within the reducing environment of the cell. In this case, the molecular scaffold (eg. TBMB) could be added during the chemical synthesis of the first peptide so as to react with the three cysteine groups; a further cysteine could then be appended to the N-terminus of the first peptide, so that this cysteine only reacted with a free cysteine of the second peptide.

Similar techniques apply equally to the synthesis/coupling of two bicyclic macrocycles. Furthermore, addition of other functional groups or effector groups may be accomplished in the same manner, using appropriate chemistry, coupling at the N- or C-termini or via side chains. Suitably the coupling is conducted in such a manner that it does not block the activity of either entity.

In one aspect, the molecular scaffold may be replaced in the synthesised molecule with another scaffold which is structurally equivalent. In such an embodiment, the structure of the peptide ligand, and therefore its specificity, preferably does not change.

The advantage of this approach is that alternative chemistries can be introduced which may be advantageous in a clinical or other setting, or may be less costly, but cannot be contemplated in the context of biological selection. For example, when using phage, chemical manipulation is subject to constraints as it may affect phage infectivity. Such constraints may be removed when the peptide ligand is synthesised, since phage infectivity is no longer an issue.

(B) Repertoires of Peptide Ligands
(i) Construction of Libraries

Libraries intended for selection may be constructed using techniques known in the art, for example as set forth in WO2004/077062, or biological systems, including phage vector systems as described herein. Other vector systems are known in the art, and include other phage (for instance, phage lambda), bacterial plasmid expression vectors, eukaryotic cell-based expression vectors, including yeast vectors, and the like.

Non-biological systems such as those set forth in WO2004/077062 are based on conventional chemical screening approaches. They are simple, but lack the power of biological systems since it is impossible, or at least impracticably onerous, to screen large libraries of peptide ligands. However, they are useful where, for instance, only a small number of peptide ligands needs to be screened. Screening by such individual assays, however, may be time-consuming and the number of unique molecules that can be tested for binding to a specific target generally does not exceed $10^6$ chemical entities.

In contrast, biological screening or selection methods generally allow the sampling of a much larger number of different molecules. Thus biological methods are more suitably used in application of the invention. In biological procedures, molecules are assayed in a single reaction vessel and the ones with favourable properties (i.e. binding) are physically separated from inactive molecules. Selection strategies are available that allow to generate and assay simultaneously more than $10^{13}$ individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

When using a biological system, once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected before mutagenesis and additional rounds of selection are performed.

Such approaches are particularly indicated for affinity maturation of peptide ligands as described herein. Foe example, a first and a second repertoire of peptide ligands which bind to a first and second target may be combined, and the resulting third repertoire subjected to affinity maturation by mutagenesis of the nucleic acid library members which encode the repertoire.

Mutagenesis of nucleic acid sequences encoding structurally optimised polypeptides is carried out by standard molecular methods. Of particular use is the polymerase chain reaction, or PCR, (Mullis and Faloona (1987) Methods Enzymol., 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

PCR is performed using template DNA (at least 1fg; more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4, µl of 1.25 µM dNTP, 0.15 µl (or 2.5 units) of Taq DNA polymerase (Perkin Elmer, Foster City, Calif.) and deionized water to a total volume of 25 µl. 1. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenized, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99 C for 15 seconds to 1 minute), annealing (temperature determined as discussed above; 1-2 minutes), and extension (72° C. for 1-5 minutes, depending on the length of the amplified product). Final extension is generally for 4 minutes at 72° C., and may be followed by an indefinite (0-24 hour) step at 4° C.

Alternatively, given the short chain lengths of the polypeptides according to the invention, the variants are preferably synthesised de novo and inserted into suitable expression vectors. Peptide synthesis can be carried out by standard techniques known in the art, as described above. Automated peptide synthesisers are widely available, such as the Applied Biosystems ABI 433 (Applied Biosystems, Foster City, Calif., USA)

(ii) Genetically Encoded Diversity

The polypeptides of interest are suitably genetically encoded. This offers the advantage of enhanced diversity together with ease of handling. An example of a genetically encoded polypeptide library is a mRNA display library. Another example is a replicable genetic display package (rgdp) library such as a phage display library. Suitably, the polypeptides of interest are genetically encoded as a phage display library.

Thus, suitably the complex of the invention comprises a replicable genetic display package (rgdp) such as a phage particle. In these embodiments, suitably the nucleic acid is comprised by the phage genome. In these embodiments, suitably the polypeptide is comprised by the phage coat.

In some embodiments, the invention may be used to produce a genetically encoded combinatorial library of polypeptides which are generated by translating a number of nucleic acids into corresponding polypeptides and linking molecules of said molecular scaffold to said polypeptides.

The genetically encoded combinatorial library of polypeptides may be generated by phage display, yeast display, ribosome display, bacterial display or mRNA display.

Suitably the genetically encoded combinatorial library of polypeptides is generated by phage display. In phage display embodiments, suitably the polypeptides are displayed on phage according to established techniques such as described below. Most suitably such display is accomplished by fusion of the target polypeptide of interest to an engineered gene permitting external display of the polypeptide of interest; suitably said engineered gene comprises an engineered gene 9 (p9 or gene IX), gene 8 (gene VIII), gene 7 (p7 or gene VII), gene 6 (p6 or gene VI) or gene 3 (p3 or gene III) of the phage. These proteins offer the advantage that they contain fewer or no cysteines that can react with molecular scaffolds such as TBMB and produce side products. For p6, it is advantageous to mutate cysteine 84 to serine. The cysteines in p7 and p9 are most likely buried and therefore may not necessarily need to be mutated to remove them. p8 offers the advantage that it does not contain a cysteine residue. Thus, more suitably said engineered gene comprises an engineered gene 8 (gene VIII), gene 6 (gene VI) or gene 3 (gene III) of the phage.

Most suitably such display is accomplished by fusion of the target polypeptide of interest to an engineered gene 3 protein lacking cysteine residues in domain 1 and 2. This fusion may be accomplished by any suitable technique known in the art such as by manipulation of the nucleic acid encoding the phage gene III protein to change the codons encoding cysteine to codon(s) encoding other amino acid(s), and by inserting a nucleic acid sequence encoding the target polypeptide into the gene III coding sequence in frame so that it is displayed as a gene III fusion protein on the outside of the phage particle.

It is a benefit of the invention that the resulting engineered gene(s) leave the phage infective i.e. capable of infection and propagation. Even when the engineered gene is a gene other than gene 3, (such as gene 6 or gene 8), it may still be desirable to engineer gene 3 to remove one or more of the cysteine residue(s) (such as all of the cysteine residues).

In a preferred embodiment, the genetically encoded polypeptides of the invention are generated by translating a nucleic acid and linking the generated polypeptide to said code.

The linkage of phenotype with the genotype allows propagating or decoding the encoded ligand repertoires. Various techniques are available to link the polypeptide to its polynucleotide code. The techniques include phage display, ribosome display, mRNA display, yeast display and bacterial display and others. Encoded polypeptide repertoires comprising up to 10exp13 individual members have been generated with said methods. The number of individual ligands that can be generated according to the invention outperforms clearly the number of individual molecules that are generally assayed in conventional screens.

In a preferred embodiment, phage display technology is used to genetically encode polypeptides of the invention. Phage display is a method in which the gene of a polypeptide is fused to the gene of a phage coat protein. When phage are produced in a bacterial cell, the polypeptide is expressed as a fusion of the coat protein. Upon assembly of a phage particle the polypeptide is displayed on the surface of the phage. By contacting a phage repertoire with an immobilized antigen some phage remain bound to the antigen while others are removed by washing. The phage can be eluted and propagated. The DNA encoding the polypeptide of selected phage can be sequenced. Phage display can be used to encode more than $10^{10}$ individual polypeptides. A favourable aspect of phage display is that the genetic code, a single stranded DNA is packed in a coat. The coat may protect the DNA from reaction with the molecular core.

In another preferred embodiment, the polypeptide library of the invention is displayed on phage as a gene 3 protein fusion. Each phage particle has about 3 to 5 copies of said phage coat protein. As a result of the display of multiple copies of the modified polypeptide, ligands with micromolar affinities (weak binders) can also be isolated in phage selections. Alternatively, phagemids are used to reduce the number of polypeptides per phage to avoid avidity effects and select ligands with higher affinities.

In another preferred embodiment, phage with modified coat proteins are used for encoding the polypeptide libraries of the invention. In particular, phage lacking or having a reduced number of a specific type of amino acid in coat proteins are used. Using said coat proteins can be advantageous when the molecular core is reactive towards said specific type of amino acid. This is explicitly the case when the reactive groups of the displayed polypeptide for cross-linking a molecular core are natural amino acids and the same type of natural amino acid is present at a surface exposed region in the phage coat. Using said phage with modified coat proteins can prevent cross-linking of phage particles through reaction of amino acids of multiple phage with the same molecular core. In addition, using said phage can reduce the cross-linkage of both, amino acid side chains of the reactive groups in the polypeptide and of phage coat protein to the same molecular core.

In yet another preferred embodiment, phage with a gene 3 protein lacking the cysteine residues of the disulfide bridges C7-C36, C46-C53, C188-C201 in domain 1 and 2 are used to display polypeptide libraries of the invention. A phage with mutations in said positions (C7C, C36I, C46I, C53V, C188V, C201A) and 14 additional mutations in the gene 3 protein to compensate for the reduced thermal stability (T13I, N15G, R29W, N39K, G55A, T56I, I60V, T101I, Q129H, N138G, L198P, F199L, S207L, D209Y) was generated by Schmidt F. X. and co-workers (Kather, I. et al., J. Mol. Biol., 2005). Phage without thiol groups in said minor coat protein are suited if one or more of the functional amino acids for cross-linking the polypeptide to a molecular core are cysteine residues. Removal of the cysteine residues in the phage coat protein prevents their interference with said bonding reaction between polypeptide and molecular scaffold.

This exemplary phage for application in the invention is now described in more detail.

The disulfide-free phage of F X Schmid (domains D1-D2) comprises fd phage derived from vector fCKCBS (Krebber, C., 1997, J. Mol. Biol.). The vector fCKCBS is based on a fd phage vector that is derived from the American Type Culture Collection (ATCC: 15669-B2).

The amino acid sequence of the domains 1 and 2 of p3 of the wild-type fd phage is publicly available, for example in the PubMed database. For ease of reference, an exemplary sequence is:

(SEQ ID No. 3)
AETVESCLAKPHTENSFTNVWKDDKTLDRYANYEGCLWNATGVVVCTGD

ETQCYGTWVPIGLAIPENEGGGSEGGGSEGGGSEGGGTKPPEYGDTPIP

GYTYINPLDGTYPPGTEQNPANPNPSLEESQPLNTFMFQNNRFRNRQGA

LTVYTGTVTQGTDPVKTYYQYTPVSSKAMYDAYWNGKFRDCAFHSGFNE

DPFVCEYQGQSSDLPQPPVNAPSG

FX Schmid and co-workers had evolutionarily stabilized the p3 of this phage (Martin, A. and Schmid, F X., 2003, J. Mol. Biol.) by mutating 4 amino acids. In a consecutive work FX Schmid and co-workers had mutated 6 cysteines to eliminate the 3 disulfide-bridges and inserted additional mutations to compensate for the loss of stability (Kather, I. and Schmid F X., 2005, J. Mol. Biol.). In multiple evolutionary cycles they had generated clones 19, 20, 21, and 23 which have all a disulfide-free p3 with varying thermal stabilities.

The mutant 21 ('clone 21') can be made as described, or simply obtained from F X Schmid and co-workers. According to the publication of F X Schmid this clone contains the following mutations in the domains 1 and 2: C7S, T13I, N15G, R29W, C36I, N39K, C46I, C53V, G55A, T101I, Q129H, C188V, F199L, C201A, D209Y. In addition we found the following mutations in the domains 1 and 2 when we sequenced the clone and compared it to wild-type fd phage: P11S and P198L. Without wishing to be bound by theory it is assumed that these mutations were already present in the phage of vector fCKCBS.

The domains D1 and D2 of clone 21 have the following amino acid sequence:

(SEQ ID No. 4)
AETVESSLAKSHIEGSFTNVWKDDKTLDWYANYEGILWKATGVVVITGD

ETQVYATWVPIGLAIPENEGGGSEGGGSEGGGSEGGGTKPPEYGDTPIP

GYIYINPLDGTYPPGTEQNPANPNPSLEESHPLNTFMFQNNRFRNRQGA

LTVYTGTVTQGTDPVKTYYQYTPVSSKAMYDAYWNGKFRDVAFHSGFNE

DLLVAEYQGQSSYLPQPPVNAPSG

In one embodiment, screening may be performed by contacting a library of the invention with a target and isolating one or more library member(s) that bind to said target.

In another embodiment, individual members of said library are contacted with a target in a screen and members of said library that bind to said target are identified.

In another embodiment, members of said library are simultaneously contacted with a target and members of said library that bind to said target are selected.

The target(s) may be a peptide, a protein, a polysaccharide, a lipid, a DNA or a RNA.

The target may be a receptor, a receptor ligand, an enzyme, a hormone or a cytokine.

The target ligand may be a prokaryotic protein, a eukaryotic protein, or an archeal protein. More specifically, the target ligand may be a mammalian protein or an insect protein or a bacterial protein or a fungal protein or a viral protein.

The target ligand may be an enzyme, such as a protease.

It should be noted that the invention also embraces library member(s) isolated from a screen according to the invention. Suitably the screening method(s) of the invention further comprise the step of: manufacturing a quantity of the complex of the invention isolated as capable of binding to said targets.

The invention also relates to library members which are, or are capable of being, isolated by a screen according to the present invention, wherein said member is subsequently generated/manufactured without the further use of the nucleic acid which encoded said polypeptide when part of the complex of the invention. For example, the methods of the invention suitable further comprise the additional step of manufacturing a quantity of a polypeptide isolated or identified by a method of the invention by attaching the molecular scaffold to the polypeptide, wherein said polypeptide is recombinantly expressed or chemically synthesized. For example, when the polypeptide is recombinantly synthesised in this embodiment, the nucleic acid originally encoding it as part of a complex of the invention may no longer be directly present but may have been present in an intermediate step eg. PCR amplification or cloning of the original nucleic acid of the complex, leading to production of a template nucleic acid from which the polypeptide may be synthesised in this additional step.

Polypeptide ligands may have 1 2 or more more than two loops. For example, tricyclic polypeptides joined to a molecular scaffold can be created by joining the N- and C-termini of a bicyclic polypeptide joined to a molecular scaffold according to the present invention. In this manner, the joined N and C termini create a third loop, making a tricyclic polypeptide. This embodiment is suitably not carried out on phage, but is suitably carried out on a polypeptide-molecular scaffold conjugate of the invention. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N—C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degredation of the free ends, in particular by exoprotease action. Another advantage of a tricyclic polypeptide of this nature is that the third loop may be utilised for generally applicable functions such as HSA binding, cell entry or transportation effects, tagging or any other such use. It will be noted that this third loop will not typically be available for selection (because it is not produced on the phage but only on the polypeptide-molecular scaffold conjugate) and so its use for other such biological functions still advantageously leaves both loops 1 and 2 for selection/creation of specificity. Thus the invention also relates to such tricyclic polypeptides and their manufacture and uses.

The present invention provides further methods for contacting the genetically encoded compound libraries with a target ligand and for identifying ligands binding to said target ligand. The genetically encoded compound libraries are assayed by either screening or selection procedures.

In a screening procedure, individual members of the library are assayed. Multiple copies of an individual member of the library are for example incubated with a target ligand. The target ligand is immobilized before or after contacting the members of the library and unbound members are removed by washing. Bound ligands are for example detected in an enzyme linked immunosorbent assay (ELISA). The amino acid sequences of members of the library that bind to the target ligand are determined by sequencing of the genetic code.

In a selection procedure, multiple members of the encoded compound library are contacted with one or more targets. The targets are immobilized before or after contacting the members of the library and unbound members are removed by washing. The genetic code of bound ligands is sequenced. Selected ligands are alternatively propagated to perform further selection rounds.

In one embodiment of the invention, the compound libraries are encoded by phage display and selections are performed by phage panning.

(iii) Phage Purification

Any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously.

In case further guidance is needed, reference is made to Jespers et al (Protein Engineering Design and Selection 2004 17(10):709-713. Selection of optical biosensors from chemisynthetic antibody libraries.) Suitably phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol. vol 222 pp 581-597, which is specifically incorporated herein by reference for the particular description of how the phage production/purification is carried out.

In case any further guidance is needed, phage may be reduced and purified as follows. Approximately $5\times10^{12}$ phage particles are reacted with 1 mM dithiothreitol (DTT) for 30 min at room temperature, then PEG precipitated. After rinsing with water, the pellet is resuspended in 1 ml of reaction buffer (10 mM phosphate buffer, 1 mM EDTA, pH 7.8). The phage are then optionally reacted with 50 μl of 1.6 mM N-[(2-iodoacetoxy)ethyl]-N-methylamino-7-nitrobenz-2-oxa-1,3-diazole (NBDIA) (Molecular Probes) for 2 h at room temperature, or more suitably reacted with the molecular scaffold as described herein. The reaction is terminated by PEG precipitation of phage particles.

A yet still further way in which the phage may be produced/purified is as taught in Schreier and Cortese (A fast and simple method for sequencing DNA cloned in the single-stranded bacteriophage M13. Journal of molecular biology 129(1):169-72, 1979). This publication deals with the chain termination DNA sequencing procedure of Sanger et al. (1977), which requires single-stranded DNA as template. M13 phage DNA exists as a single strand and therefore every DNA sequence cloned in M13 can be easily obtained in this form. Schreier and Cortese show that M13 single-stranded DNA pure enough to be used as a template for sequence determination can be prepared by simple centrifugation of the phage particle and extraction with phenol. The Schreier and Cortese publication is specifically incorporated herein by reference for the method of purification of the phage. For the avoidance of doubt, the phenol extraction is not performed for making complexes according to the present invention since that is for the purpose of nucleic acid purification. Thus the phenol step of Schreier and Cortese is suitably omitted. The Schreier and Cortese method is followed only to the point of purified phage particles.

Thus there are myriad techniques well known in the art for purification of phage. In the context of the present invention such purification is used for the removal of reducing agent used to reduce the reactive groups in the polypeptide of interest for bonding to the molecular scaffold, particularly when such bonding is via cysteine residues.

Optionally, especially advantageous techniques for phage purification may be adopted as discussed in the reaction chemistry section below. It should be expressly noted that these techniques are not regarded as essential for the invention, but may represent especially helpful methods or even the best mode of making the phage particles of the invention. However, provided attention is paid to avoiding reoxidation of the reduced functional/reactive groups on the phage at the stage of removal of the reducing agent before attachment of the molecular scaffold then in principle any technique may be used to accomplish this. The filtration techniques described are particularly effective but also more complicated than standard techniques so the operator will choose the technique best suited to their particular working of the invention. Most suitably the filtration technique is employed.

(iv) Reaction Chemistry

Prior art technologies for modification of polypeptides have involved harsh chemistry and independent polypeptide modification reactions. By contrast, the present invention makes use of chemical conditions for the modification of polypeptides which advantageously retain the function and integrity of the genetically encoded element of the product. Specifically, when the genetically encoded element is a polypeptide displayed on the surface of a phage encoding it, the chemistry advantageously does not compromise the biological integrity of the phage. It is disclosed herein that there is a narrow window of conditions for which these chemical reactions can be enhanced or facilitated. In particular, as will be explained in more detail below, the solvents and temperatures used are important to an efficient reaction. Furthermore, the concentration of the reagents used are also instrumental in promoting the correct bonding, whilst ameliorating or eliminating cross linking or damaging of the polypeptide moieties which are being modified.

In particular, it is disclosed that the reduction of the cysteines in the target polypeptide is required for the most efficient reaction. Clearly, the reducing agent used to chemically reduce those cysteines must be removed in order to perform the desired attachment. One known technique is to use dithiothreitol (DTT) or triscarboxyethylphosphine (TCEP) for reduction of the cysteines, and for the removal of the reducing agent to precipitate the particles such as the phage particles in a precipitation reaction. Such precipitation reactions typically involve 20% polyethylene glycol (PEG) together with 2.5 molar NaCl which leads to precipitation of the phage particles. However it is important to avoid re-oxidation. As will be disclosed in more detail below, the solutions are found in a range of strategies including the use of degassed buffer, the use of chelators in the reaction mixture, and the use of filtration in order to extract the particles, or the use of low concentrations of TCEP in the presence of TBMB.

Reaction conditions e.g. for attachment of the molecular scaffold to the target polypeptide should be chosen carefully. Choice of conditions may vary depending upon the application to which the invention is being put. Particular care is required when the target polypeptide is comprised by a phage particle. Guidance is provided throughout the specification and examples section.

Reaction conditions as reaction temperature, molecular scaffold concentration, solvent and/or pH should be chosen to allow efficient reaction of the reactive groups of the target polypeptide with the molecular scaffold, but leave the nucleic acid encoding the polypeptide in a condition that allows to decode (e.g. to sequence) and/or propagate the isolated molecules (e.g. by PCR or by phage propagation or any other suitable technique). Moreover, the reaction conditions should leave the phage coat protein in a condition that allows it to propagate the phage.

Thiol groups of a phage encoded polypeptide may be reduced with reducing agent prior to molecular scaffold attachment. In such embodiments, in particular in phage display embodiments, or in particular when the reducing agent is TCEP, the excess of reducing agent is suitably removed by filtration e.g. filtration of the phage. This is especially advantageous since the present inventors disclose for the first time that conventional techniques for removal of reducing agents such as PEG/NaCl precipitation can sometimes lead to sub-optimal reaction with molecular scaffold, likely due to reoxidation of the reduced functional side groups of the target polypeptide. Thus it is an advantage of embodiments in which the target polypeptide is prepared by reduction followed by purification (removal of reducing agent) via filtration that superior preservation of the reduced (and hence reactive) reactive groups of the polypeptide is achieved.

In the present invention, reaction conditions are applied that on the one hand allow to efficiently link the encoded polypeptide to a molecular scaffold and on the other hand leave the appended nucleic acid (and phage coat proteins) in a condition that allows its propagation or decoding. Said reaction conditions are for example the reaction temperature, molecular scaffold concentration, solvent composition or pH.

In one embodiment of the present invention, thiol groups of cysteine residues are used as reactive groups to link polypeptides to a molecular core. For some chemical reactions, the thiol groups of the polypeptides need to be reduced. Thiol groups in phage displayed polypeptides are efficiently reduced by addition of a reducing agent as for example tris(carboxyethyl)phosphine (TCEP). Since an excess of reducing agent can interfere with the attachment reaction it is largely removed by filtration of the phage, or by PEG precipitation, although low concentrations (10 micromolar or less) may be desirable to maintain reducing conditions during the attachment reaction.

Re-oxidation of the thiol groups after removal of TCEP is suitably prevented by degassing of the reaction buffer.

Re-oxidation of the thiol groups is also suitably prevented by complex formation of metal ions by chelation, for example chelation with ethylenediaminetetraacetic acid (EDTA).

Most suitably re-oxidation of the thiol groups is prevented or inhibited by both chelation and use of degassed buffers.

In one embodiment of the present invention, attachment of the polypeptide to the molecular scaffold is accomplished by reacting the reactive groups of the polypeptide such as thiol groups of a phage encoded polypeptide with the molecular scaffold for one hour.

Suitably they are reacted at 30° C.

Suitably they are reacted with molecular scaffold (such as tris(bromomethyl)benzene) at a concentration of 10 µM.

Suitably reaction is in aqueous buffer.

Suitably reaction is at pH 8.

Suitably reaction buffer contains acetonitrile. Suitably reaction buffer contains 20% acetonitrile.

Most suitably the reaction features two or more of the above conditions. Suitably the reaction features three or more of the above conditions. Suitably the reaction features four or more of the above conditions. Suitably the reaction features five or more of the above conditions. Suitably the reaction features six or more of the above conditions. Suitably the reaction features each of the above conditions.

These reaction conditions are optimized to quantitatively react thiol groups of a polypeptide with the reactive groups of tris(bromomethyl)benzene. Under the same reaction conditions, about 20% of the phage particles remain infective to bring the genetic code into bacterial cells for propagation and decoding.

In one embodiment the molecular scaffold, such as TBMB, may be attached to the target polypeptide, such as a phage encoded polypeptide, by reaction (incubation) of thiol groups of the polypeptide for one hour at 30° C. with TBMB (i.e. tris(bromomethyl)benzene) at a concentration of 10 µM in aqueous buffer pH 8 containing 20% acetonitrile.

The inventors also disclose the effect of concentration of the molecular scaffold in the reaction on phage infectivity. In particular the invention suitably minimises the concentration of molecular scaffold used in the reaction. In other words, the lower the concentration of molecular scaffold used at the time of reaction with the polypeptide of the phage, the better, provided always that sufficient molecular scaffold becomes joined to the phage polypeptide. The advantage of minimising the molecular scaffold present in this way is superior preservation of phage infectivity following coupling of the molecular scaffold. For example, when the molecular scaffold is TBMB, concentrations of molecular scaffold greater than 100 μM can compromise infectivity. Thus suitably when the molecular scaffold is TBMB then suitably the concentration of TBMB present at the time of bonding to the polypeptide is less than 100 μM.

(C) Use of Peptide Ligands According to the Invention

Peptide ligands selected according to the method of the present invention may be employed in in vivo therapeutic and prophylactic applications, in vitro and in vivo diagnostic applications, in vitro assay and reagent applications, and the like.

In general, the use of a peptide ligand can replace that of an antibody. Ligands selected according to the invention are of use diagnostically in Western analysis and in situ protein detection by standard immunohistochemical procedures; for use in these applications, the ligands of a selected repertoire may be labelled in accordance with techniques known in the art. In addition, such polypeptide ligands may be used preparatively in affinity chromatography procedures, when complexed to a chromatographic support, such as a resin. All such techniques are well known to one of skill in the art. Peptide ligands according to the present invention possess binding capabilities similar to those of antibodies, and may replace antibodies in such assays.

Diagnostic uses include any uses which to which antibodies are normally put, including test-strip assays, laboratory assays and immunodiagnostic assays.

Therapeutic and prophylactic uses of peptide ligands prepared according to the invention involve the administration of ligands selected according to the invention to a recipient mammal, such as a human. Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available.

Methods for the testing of systemic lupus erythematosus (SLE) in susceptible mice are known in the art (Knight et al. (1978) J. Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988) Adv. Inzn7unol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J; Immunol., 138: 179).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The polypeptide ligands of the present invention may be used as separately administered compositions or in conjunction with other agents. These can include antibodies, antibody fragments and various immunotherapeutic drugs, such as cyclosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The polypeptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present polypeptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present polypeptide ligands or cocktails thereof may also be administered in similar or slightly lower dosages.

A composition containing a polypeptide ligand according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Examples

In the following examples, we describe alterations of individual members of a first repertoire of peptide ligands; similar methods can be used make alterations of entire repertoires. In some cases it may be possible to use similar chemistry and library format for making both repertoires. Thus a first repertoire of peptide ligands conjugated through cysteine residues with trisbromomethylbenzene can be altered according to the invention to give a second repertoire of the same peptides conjugated with trisbromomethylmesitylene under similar conditions. Furthermore as the chemistry and reaction conditions are suitable for phage display, both first and second repertoire can be displayed and selected on phage.

However alterations made by conjugation with other scaffolds, for example those reacting through iodoacetyl or acryloyl moieties of the scaffold, although similar for making synthetic peptides may not be suitable for phage display; if not it will be necessary to use a different library format. One format that is tolerant to greater range of chemistries and more extreme reaction conditions is the synthetic peptide array. For reference see for example Min & Mrksich. Current Opinion in Chemical Biology, Volume 8, Issue 5, October 2004, Pages 554-558. This format is particularly convenient if the selection factor required (and therefore library size) is not large, as the number of peptides that can arrayed conveniently are in the hundreds or thousands, rather than the millions or billions that can be selected by phage display. It is therefore suitable for refinement of the properties of lead peptides, for example for improving resistance to protease, or binding affinity to target.

The synthetic peptide array is also a highly suitable format for reacting with multiple scaffold species; in this way the same set of peptides can be used with different scaffold species to increase the structural diversity of the second repertoire. The use of synthetic peptides is also highly suitable for alterations of the reactive group of the peptide to those not normally incorporated during biological peptide synthesis, for example the alteration of cysteine to homocysteine.

If phage display can be used for creation of both first and second repertoires, it is not necessary (or convenient) to determine the sequence of each member of the first repertoire in order to make the alterations required to generate the second repertoire. However, if however phage display is used for the first repertoire, and a synthetic peptide array for the second repertoire, it will be necessary to determine the polypeptide sequences of the first repertoire in order to specify those of the second repertoire. In this case the phage nucleic acid encoding the region of each of the displayed peptide conjugates can be readily sequenced.

The invention is further described with reference to the following examples.

Examples

Example 1 Protease Resistant Bicyclic Peptide Against MDM2

MDM2 is an enzyme (an E3 ubiquitin ligase) that recognises the trans-activation domain of p53, the tumour suppressor, leading to ubiquitinylation and degradation of p53 by the proteasome. A nutlin inhibitor of the p53-MDM2 interaction can lead to in vivo activation of the p53 pathway, and it has been suggested that such agents may have potential as anti-cancer agents. Here we describe the selection of two bicyclic peptides (PEP10 and PEP48) against MDM2, a target "antigen". The affinity of each synthetic peptide was in the range 250-750 nM.

Protocols generally followed those described earlier in Heinis et al., 2009, Nature Chemical Biology 5, 502-507, unless otherwise indicated. In the work of Heinis et al., both targets, kallikrein and cathepsin G, were proteases, and the kallikrein inhibitor is fairly resistant to proteolysis by kallikrein, although it includes a kallikrein cleavage site. MDM2 is not a protease, and therefore it was not clear whether the selected peptides would also be resistant to protease. For this, and other reasons (for detail see below), we included one or more protease (chymotrypsin) steps after reaction of the phage peptide repertoires with the TBMB (including under reducing conditions) and before selection of the repertoire against MDM2. The two selected phage peptides PEP10 and PEP 48 appear resistant to proteolysis, as shown by phage ELISA.

Phage Production and Purification

The phage peptide library with diversity of at least $4 \times 10^9$ clones was prepared and TBMB conjugated as described earlier with a few modifications.

1. The cx6 library of phage as described earlier (which had been prepared from TG1 cells) was used to infect the non-suppressor strain HB2151 (Carter, Bedouelle & Winter. 1985. Nucleic Acids Res. 13:4431-43), and the infected cells plated. The bacteria were scraped from the plates in about 8 ml 2×TY medium, 30 ug/ml chloramphenicol, 10% glycerol (v/v).
2. About 0.8 ml of the stock was added to 800 ml 2×TY medium with 30 ug/ml chloramphenicol to obtain an OD of about 0.1 at 600 nm. The culture was incubated at 30° C., and shaken in a 2 liter flask at 200 rpm for 16 hrs.

3. The cell culture was centrifuged at 4,000 rpm (Heraeus Megafuge 2R) for 30 min at 4° C. The supernatant was transferred to 200 ml cold 20% PEG, 2.5 M NaCL. The mixture was left on ice for 1 hr.
4. The precipitated supernatant/phage mixture was spun down for 30 min at 4° C. and the supernatant was discarded.
5. The phage was resuspended in 35 ml PBS, 5 mM EDTA followed by spinning for 15 min at 4000 rpm (Heraeus Megafuge 2R) to remove cellular debris. The supernatant was transferred into a new 50 ml Falcon tube.

Modification of Phage with TBMB
1. 5 ml of 8 mM TCEP (in $H_2O$) was added to the phage to obtain a final concentration 1 mM TCEP. The tube was inverted several time to mix and incubated for 1 hr at 42° C. water bath.
2. The TCEP was removed by a second PEG precipitation. 10 ml of 20% PEG, 2.5 M NaCL (degassed solution) was added, mixed, and incubated on ice for 45 min and spun for 30 min at 4000 rpm, 4° C.
3. The supernatant was carefully removed and pellet resuspended in 12 ml PBS, 5 mM EDTA, 10 uM TCEP (degassed buffer)
4. 3 ml of 50 uM TBMB in acetonitrile was added to the 12 ml of reduced phage to obtain a final TBMB concentration of 10 uM. The tube was inverted several times and left at 30° C. for 1 hr in a water bath. The phage were cooled on ice and precipitated with 1/5 volume of 20% PEG, 2.5 M NaCL for 30 min. The phage were collected by spinning at 4000 rpm (Hereaus Megafuge 2R) for 20 min. Supernatant was removed and the phage resuspended in 4 ml of PBS. Phage was transferred into the 2 ml Eppendorf tubes and spun at 13000 rpm (Eppendorf benchtop centrifuge) for 10 min. Supernatant was transferred into a new Eppendorf tube and phage infectivity was measured.

Phage Selection: General Protocol
First Round of Selection
1. Purified and chemically conjugated phage as above was selected against biotinylated MDM2 (bio-MDM2) peptide (res 2-125) immobilized on the surface of the streptavidin-coated Dynabeads (Dynal Biotech). 80 μl of beads were first washed and blocked with 2% (w/v) Marvell milk powder in PBS (PBSM) for 40 min followed by incubation with 100 nM bio-MDM2 for 20 min in a total volume of 1 ml.
2. Chemically modified phage ($10^{10}$-$10^{11}$TU) was incubated with PBSM for 40 min.
3. Blocked Ag-coated beads from step 1 were washed from the excess of the Ag with 0.1% Tween in PBS (PBST) and incubated with the blocked phage for 30 min in a total volume of 1 ml.
4. Unbound phage were washed with 10× with PBST followed by 2× with PBS. After each third washing step the phage coated beads were transferred into a new Eppendorf tube.
5. Phage were eluted by incubating with 500 μl of 50 mM glycine pH 2.2 for 10 min on a rotating wheel. Eluted phage were neutralized with 250 μl of 1M Tris, pH7.5.
6. 375 μl of phage was incubated with 10 ml of HB2151 cells for 90 min at 37° C. without shaking.
7. The infected cells were then shaken for 30 min at 37° C. and then plated on a chloramphenicol plate (20×20 cm).
8. The colonies were scraped off the plate in 2×TY, chloramphenicol, 10% glycerol as described above, and stored as a glycerol stock at −80° C. A fraction of the cells was used to prepare phage for the second round of selection.

Second Round of Selection
The second round of selection was similar to the first one except for a few modifications.
1. Neutravidin-coated magnetic beads were used instead of streptavidin ones.
2. The amount of antigen used in the selection was 20 nM.
3. Chemically modified phage ($10^{10}$-5×$10^{10}$ TU) was first treated with 50 ug/ml of chymotrypsin for 2 min followed by blocking with PBSM for 40 min.
4. Unbound phage was washed with 15× with PBST followed by 2× with PBS, otherwise as above.

Phage Selection: Variant Protocol
Clone 48 was selected using the general protocol as above, whereas clone 10 was developed as a result of a modified protocol being introduced. The modifications are the following:
1. In the first round chemically modified phage were pre-treated with 50 ug/ml of chymotrypsin for 2 min followed by blocking with PBSM for 40 min.
2. In the second round chemically modified phage were first reduced with 5 mM DTT for 20 min followed by incubation with 50 ug/ml of chymotrypsin for 2 min and blocking with PBSM for 40 min.

Peptide Synthesis
The encoded peptides from phage clone 48 and phage clone 10 were synthesized with free N- and C-termini.
PEP10: H-Ser-Cys-Glu-Leu-Trp-Asn-Pro-Lys-Cys-Arg-Leu-Ser-Pro-Phe-Glu-Cys-Lys-Gly-OH (SEQ ID No. 5);
PEP48: H-Ser-Cys-Val-Arg-Phe-Gly-Trp-Thr-Cys-Asp-Asn-Ser-Trp-His-Gly-Cys-Lys-Gly-OH (SEQ ID NO. 6).

The syntheses were performed employing Fmoc chemistry on a CEM Liberty microwave peptide synthesizer at a 0.1 mmol scale. Fmoc-Gly-PEG PS resin using a 5-fold excess of Fmoc-amino-acids activated with PyBOP in DMF and DIPEA in NMP (1 equivalent and 2 equivalents respectively. Side-chain protecting groups were as follows: Arg(Pbf); Asn(Trt); Asp(OtBu); Cys(Trt); Glu(OtBu); Lys(Boc); Ser (tBu); Thr(tBu); Trp(Boc). Fmoc-deprotection was carried out using 20% v/v Piperidine/DMF containing 0.1M HOBt. The H-peptidyl-resins were washed with DMF, then propan-2-ol and dried in vacuo. Cleavage of side-chain protecting groups and from the support was effected using 94:2.5:2.5:1 v/v/v/v TFA/EDT/$H_2O$/$iPr_3$SiH for 2 hours. The peptide/TFA mixture was filtered to remove the support and the peptide/TFA mixture was diluted with water and washed with $Et_2O$ (5-times) and the aqueous layer lyophilized.

Reverse-phase HPLC was performed on a Phenomenex Jupiter 5μ C18 300 Å 250×4.6 mm column. Buffer A: 0.1% TFA/H20; Buffer B: CH3CN containing 10% Buffer A. The column was eluted isocratically with 10% Buffer B for 2 minutes, then with a linear gradient of 10-90% over 25 minutes. Detection was at 215/230 nm; flow rate of 1.5 ml/min.

The peptides were lyophilized and checked by mass spectrometry. PEP10 MALDI-TOF mass (M+H): 2099.9 Da (Theory: 2098.4 Da.) PEP48 MALDI-TOF Mass (M+H): 2043.8 Da (Theory: 2042.8 Da.). The peptides were then conjugated with TBMB.

Synthesis of TBMB-Peptide Conjugates
Initial reactions were performed to mimic the conditions used during phage selection. Typically, 5 mg of the purified peptide was dissolved in 1 ml water and 0.8 ml 50 mM $NH_4HCO_3$ added, followed by enough TCEP to bring the final concentration to 10 m TCEP. TBMB (3 equivalents based on weight of peptide) dissolved in MeCN was added to the reaction. The reaction was left for 1.5 hrs then monitored by HPLC. On completion the reaction was purified by HPLC. Typically 0.5 to 1.5 mg of final product was obtained. However this method gives rise to several by-products, the major one having an additional mass of +250 Dalton. This corresponds to addition of TCEP to the desired product, and the yield of this product increases with reaction time. In addition, other higher mass products corresponding to addition of a second TBMB were observed by MALDI-TOF mass spec, but were not isolated.

Based on the formation of TCEP adducts a preferred method was developed. Following cleavage of the peptide from the resin, it was either purified directly by HPLC or pre-treated with TCEP/DTT for 15 mins prior to HPLC purification. The product from the HPLC purification, in the HPLC elution buffer (typically 6 ml) is neutralised with 50 mM $NH_4HCO_3$ (4 ml) and TBMB added in MeCN as above. The addition of 10% THF results in a clear solution and therefore accelerates the reaction. Reactions are monitored by mass spec, but typically are complete in 1-2 hrs. There are minimal by-products from this reaction (though the presence of product +16 is observed by mass spec). The reaction requires concentration to remove organic solvents prior to HPLC purification otherwise the product tends to elute with the solvent front. Yields of product from this method are typically 0.5 to 1.5 mg from 3 mg peptide, but this has not been optimised.

Binding Assays

Phage ELISA Assay 0.6 μg/mL of biotinylated MDM2 peptide (res 2-125) was immobilised on a streptavidin-coated plate (Roche). Plate was blocked with PBSM (but 4% in milk powder) and linear or TBMB-conjugated phage ($10^7$ TU/well in PBSM in the presence or absence of 5 mM DTT) was incubated on the plate for 50 min at room temperature. Similarly, phage was first reduced in 5 mM DTT for 20 min, treated with chymotrypsin (50 ug/ml in PBS) for 2 min, mixed with PBSM (final concentration) and incubated on the plate for 50 min at room temperature. Phage was detected using an anti-M13-HRP monoclonal antibody (1:5000, Amersham).

The results showed qualitatively that both phage clones 10 and clone 48 bind to MDM2 as the cyclic conjugate but not as the unconjugated peptide (whether or not pre-treated with DTT). Furthermore the binding of the conjugated peptide resists proteolysis. Note that 5 mM DTT can reduce the disulphide bonds of chymotrypsin leading to its inactivation as a protease. To ensure that the chymotrypsin was active under the conditions of the assay, we incubated control phage bearing a linear peptide that binds MDM2 after pre-treatment as above with 5 mM DTT. Under the conditions of our experiment, the binding activity of the control phage was lost on proteolysis. In other experiments we have used up to 0.2 mM-5 mM TCEP in the presence of chymotrypsin (0.1 mg/ml-1 mg/ml) for 2 minutes at room temperature in PBS. These conditions also allowed us to distinguish between the linear and cyclic peptides on phage.

Fluorescence Anisotropy Measurements

Titration experiments were run on a Horiba Jobin Yvon fluorimeter equipped with the Hamilton Microlab titrator controlled by laboratory software. The $\lambda_{ex}$ and $\lambda_{em}$ used were 295 nm and 350 nm, respectively. The slit widths for excitation and emission were 5 nm and 15 nm and the integration time 10 s was used for each measurement. The intrinsic fluorescence of tryptophan in peptides 10, 48 was used to measure their binding affinity for MDM2 (res 2-125). The experiments were performed at 23° C. in PBS, 5 mM DTT. Usually 250 μl of MDM2 (150 micromolar) was titrated into 1.2 ml of peptide (1 micromolar). Titration data were analyzed with a standard 1:1 binding model by using the quadratic solution to the equilibrium Kd=[A][B]/[AB]. Kd is the dissociation rate, and [A] and [B] refer to the concentration of a titrant (MDM2) and fluorescent peptides 10 and 48, respectively. The fitting equation contained an extra term to account for linear drift.

The results (FIG. 2 and below) indicate that the affinity of each peptide is sub-micromolar, and in the range 250-750 nM. The measurements for PEP48 were repeated.

PEP10+MDM2, measured $\lambda_{ex}$=295 nm, Kd=267 nM;
PEP48+MDM2, measured $\lambda_{ex}$=280 nm, Kd=760 nM;
PEP48+MDM2, measured $\lambda_{ex}$=295 nm, Kd=567 nM Competition Assays The binding of PEP48 phage to MDM2 was competed by a peptide pMI (TSFAEYWNLLSP (SEQ ID No. 7)) that binds to MDM2 at the p53 site with a Kd=3.3 nM (Pazgier et. al., 2009 PNAS, 106, 4665-4670). 0.6 μg/ml of biotinylated MDM2 peptide (res 2-125) was immobilized on a streptavidin-coated plate (Roche). Plate was blocked with PBSM. TBMB-conjugated phage ($10^7$ TU/well in 1% PBSM) was premixed with a range of concentrations of pDI (from 6.94 nM to 1 uM) and incubated on the plate for 75 min at room temperature. Phage was detected using an anti-M13-HRP monoclonal antibody (1:5000, Amersham). The binding of PEP48 phage to MDM2 was inhibited by addition of the pMI peptide, with an estimated IC50=125 nM.

Example 2 Oxidation of PK15-TBMB Conjugate to its Sulfoxide and Sulfone

PK15-TBMB was synthesised as described in Heinis et al., 2009, Nature Chemical Biology 5, 502-507. Approximately 1 mg of PK15-TBMB was dissolved in 1 ml of 1×PBS and hydrogen peroxide added to a concentration of 0.3%. Reaction left at room temperature overnight. MALDI mass spec showed a range of peaks corresponding to the addition of 1, 2 and 3 oxygen atoms, but incomplete reaction. Reaction adjusted to 1% $H_2O_2$ and left for 8 hrs where it could be seen that the +3 (oxygen) product was major but the reaction was still incomplete. The reaction was heated in a microwave synthesiser, initially cooled on ice, up to a temperature of 37° C., with a power of up to 50 W. After 15 mins mass spec showed essentially a single peak at 1992 corresponding to addition of 3 oxygen atoms, and therefore corresponding to the sulphoxides. There is virtually no sign of addition of further oxygen atoms under these conditions. HPLC showed essentially a single peak.

The oxidised derivative was compared for its ability to inhibit kallikrein.

Enzymes were purchased from Sigma Aldrich and substrates from Bachem AG. The assay buffer is composed of 10 mM Tris pH 7.4, 150 mM NaCl, 10 mM $MgCl_2$, 1 mM $CaCl_2$, 0.1% BSA, 0.01% Triton X100 and 5% DMSO. Enzymes are incubated with inhibitors for 30 minutes at RT prior to addition of substrate. All experiments were recorded at 30° C. for 90 minutes.

Assays were performed on a BMG Pherastar plate reader at wavelengths of exc/em 350/450 nm. Kallikrein was bought as a solution of 1080 μg/mL and diluted to a working concentration of 0.3 nM in assay buffer. Substrate Z-Phe-Arg-AMC was solubilised at the stock concentration of 10 mM in DMSO and diluted to a working concentration of 300 μM with assay buffer. Inhibitors were solubilised in assay buffer to a stock concentration of 60 μM. 50 μL of each reagent is introduced in wells for a final volume of 150 µL per well. Final concentration of kallikrein in assay is 0.1 nM and substrate is 100 µM.

Final concentrations of inhibitors were: 0.5 nM, 1 nM, 2 nM, 5 nM, 8 nM, 10 nM, 20 nM, 50 nM, 80 nM, 100 nM, 200 nM, 500 nM, 800 nM, 1 µM, 2 µM, 5 µM, 8 µM, 10 µM and 20 µM. The initial rate of the reaction is obtained by plotting fluorescence=f (time) data and by fitting a linear trendline for each concentration of inhibitor. The inhibition curves are obtained by plotting initial rate=f ([I]) and $IC_{50}$ values can be evaluated.

Under conditions where PK15-TBMB inhibited kallikrein with an IC50 of 13 nM, preliminary results indicated that the oxidized PK15-TBMB inhibited kallikrein with an IC50 of about 2.4 µM. Thus the change in the nature of the attachment of core to the peptide had a dramatic effect on the affinity of the ligand. Note that the formation of sulphoxides at three sites is expected to lead to stereoisomers of the constrained peptide as the oxidation with a single atom of oxygen creates a chiral centre at the sulphur atom. The stereoisomers are likely to differ in their interactions with the target, and the IC50 value is therefore an average of the IC50 values for each of the stereoisomers.

Subsequently conditions were established for oxidation of the conjugates to the sulphone. PK15-TBMB (4 mg) was dissolved in 1 ml water and magnesium monoperoxy phthalate (10 equivalents, 10 mg in 0.5 ml water) added. The reaction was monitored by MALDI-TOF MS until completion of reaction in 45 min and then purified by HPLC. Yield 1.8 mg, molecular weight found 2038 (calculated 2038). The product was purified by HPLC. Note that in this case, the sulphur is no longer a chiral centre, and therefore a single molecular species is expected. This oxidized PK15-TBMB inhibited kallikrein with an IC50 of 1.3 micromolar. The oxidation of the sulphur is expected to change the bond angles subtended around the sulphur, and also the packing of atoms around the core. Both effects could be responsible for the alteration of binding affinity.

Example 3 Use of Trimethylmesitylene and Triethylmesitylene Cores

PK15 was conjugated with tris(bromomethyl)mesitylene under similar conditions to those described earlier with tris(bromomethyl)benzene (Heinis et al., 2009), and purified by HPLC. The conjugate was compared for its ability to inhibit kallikrein according to the procedure set forth in Example 1. Under conditions where PK15-TBMB inhibited kallikrein with an IC50 of 13 nM, preliminary results indicated that the hexamethyl benzene conjugate inhibited kallikrein with an IC50 of 150 nM. PK15 was also conjugated with tris(bromoethyl)mesitylene as above; this led to a further loss of inhibition, with an IC50 of about 400 nM. Thus the change in the nature of the core had a dramatic effect on the affinity of the ligand. In this case, the extra bulk of the three methyl or ethyl groups will likely have altered the packing around the core, and therefore the binding affinity.

Example 4 Use of Other Scaffold Cores Based on Iodoacetyl (Iac) and Acryloyl (Acr) Functionalities All scaffold precursor structures are shown in Table 1. They were then modified with thiol-reactive functionalities to yield the final scaffold, also as shown in Table 1.

The scaffold precursors trishydroxymethylethane (for THME(IAc3)), pentaerythritol (for PE(IAc4)), triethanolamine (for TEA(IAc3)), styrene R-epoxide (for TPEA (IAc3)), tris(4-formylphenyl)amine (for TPBA(IAc3)), salicylamide (TOHPT(IAc3)), cyanuric chloride and Boc-piperazine (for TPT(Acr3)) were acquired from Sigma Aldrich.

The synthesis of the precursor for TPEA(IAc3) was performed through the condensation of styrene R-epoxide with ammonia in methanol (2 M, Sigma), using microwave irradiation for enhanced reaction rates, as described in Favretto et al, and Nugent et al (Tet. Let., 2002, 43, 2581-2584; and J. Am. Chem. Soc., 1994, 116, 6142-6148, respectively). Purification of the crude (R,R,R)-tris(2-phenyl)-ethanolamine product was performed using flash column chromatography and TLC as described.

The precursor for TPBA(IAc3) (tris-(4-hydroxymethylphenyl)amine) was prepared from the commercial aldehyde (tris(4-formylphenyl)amine, 0.1 mmole) by reduction with $NaBH_4$ in 20 mL THF (1 hr at RT), quenched with 1 mL HAc (100%), and phase extracted with $DCM/H_2O$. The resultant tris-(4-hydroxymethylphenyl)amine was kept in DCM solution for further modification (see below).

The precursor tris(ortho-hydroxyphenyl)triazine was obtained by the condensation of salicylamide at 270° C. for 3 hours, as described in Johns et al (J. Org. Chem., 1962, 27 (2), pp 592-594) and Cousin et al (Bull. Soc. Chim. France 1914, (4) 15, 416). The crude yellow product (3 g) was solubilised in concentrated NaOH (aq), and precipitated with dilute sulphuric acid. The yellow precipitate was collected by centrifugation, and repeatedly washed with $H_2O$ and EtOH, then DCM, and dried. The product was then taken up in hot DMF, which upon cooling to -20° C. precipitated tris(ortho-hydroxyphenyl)triazine as small dark yellow crystal clusters.

The Boc-protected precursor for TPT(Acr3) (tris-(Boc-piperazine)-1,3,5 triazine) was prepared from cyanuric chloride and N-boc piperazine as detailed by Chouai et al (J. Org. Chem., 2008, 73 (6), pp 2357-2366). Boc removal was achieved with 6N HCl in MeOH for 12 hrs. The crude tris-piperazino-triazine was purified by standard acid/base extraction, followed by phase extraction using $DCM/H_2O$ as solvents.

Iodoacetyl and Acryloyl groups are well-established and selective thiol-reactive groups (Hermanson, Bioconjugate Techniques $2^{nd}$ edition, Academic Press, 2008). The advantage of using these groups is that they do not require an aromatic system nearby (as is the case with TBMB), thus broadening the scope and chemical space available for thiol-reactive scaffolds.

All scaffold precursors in Table 1 contain hydroxyl groups (or secondary amino groups in the case of the precursor for TPT(Acr3)). Introduction of the iodoacetyl thiol-reactive functionality onto the hydroxyl is achieved by the following two-step approach:

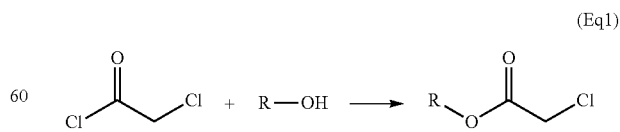

(Eq1)

(Reaction of Chloro-Acetylchloride with an Alcohol)

The purified product is then subjected to halogen exchange (Finkelstein reaction) to obtain the final iodoacetylated product:

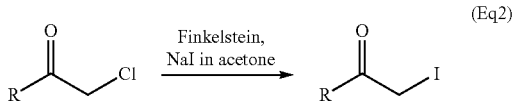
(Eq2)

The reaction with chloro-acetylchloride according to Eq1 was usually done with ~0.1 mmole scaffold precursor dissolved in 15 mL anhydrous THF. After addition of 4 equivalents of pyridine and 3.5 equivalents of chloro-acetylchloride (Sigma Aldrich), the reaction was allowed to proceed for 1-2 hours, at RT. The resultant THF-insoluble pyridine-HCl was then removed by centrifugation, and remaining chloro-acetylchloride (in theory, 0.5 equivalents) was quenched by the addition of 0.5 mL of saturated $NaHCO_3$ in $H_2O$. After rotaevaporation of the solvent, the oily product was taken up in ~10 mL acetone, and 5 equivalents of NaI (pre-dissolved at 1 M in acetone) were added (Eq2). This was reacted for up to four hours at RT. As the reaction proceeds, NaCl is precipitated, and a cessation of NaCl precipitation indicated complete replacement of all chlorines with iodines. Solvent was rotaevaporated as before, the product extracted with DCM, centrifuged to remove suspended NaCl/NaI, and washed 3 times with $H_2O$. DCM was then removed once again, and the oily orange/brown product was taken up in 10 mL acetone and stored at −20° C. in the dark.

The acryloyl group was introduced in a manner identical to Eq1, using acryloyl chloride (Cl—CO—CH=$CH_2$, Sigma Aldrich) instead.

The reaction of thiol groups with iodoacetyl groups proceeds according to:

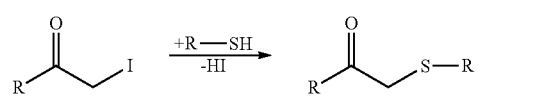
(Eq3)

The resultant HI (hydrogen iodide) is quenched by the presence of a base. The reaction of thiol groups with the acryloyl functionality proceeds according to:

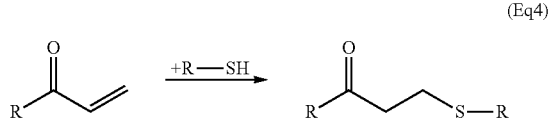
(Eq4)

Neutral to slightly basic pH is desirable for achieving selectivity towards thiols. Thus, all reactions were done with purified reduced linear 3-Cys peptide pre-dissolved in 30% acetonitrile in water, in the presence of 100 mM $NH_4HCO_3$ (~pH 8). Peptide concentrations were between 100 and 1000 mM, and scaffold concentrations were kept in slight excess (~1.5-fold). This entailed addition of the appropriate volume of acetone scaffold stock solution. Scaffold concentrations in the acetone stocks were estimated from the initial quantity of precursor employed, assuming quantitiative conversion to the iodoacetylated or acrylated derivatives, and 20% losses during the workup.

Several 3-Cys peptides, of the following sequences, were tested (cysteines are underlined):

```
Pep48-3s1    SDDCVRFGWTCPTVMCG    (SEQ ID No. 8)

Pep48-58     SDDCVRFGWTCEPSLPGCG   (SEQ ID No. 9)

Pep48-37     SDCVRFGWTCSPGMVGCD    (SEQ ID No. 10)
```

All iodoacetyl scaffolds reacted with any of the peptides very rapidly (conversion was usually complete within 10 minutes under these conditions), as judged by mass spectrometry (MALDI). As an example, the reaction of TPEA (IAc3) ((R,R,R)-tris(2-phenyl)-ethanol amine trisiodoacetate) with Pep48-58 was sampled after 5 min and analysed by MALDI.

The mass increase of 499 Da (due to addition of the scaffold, and elimination of 3 HI) correlates well with the theoretical expected value (500 Da, Table 1). Intermediate products (i.e. higher masses with an iodine atom still attached to the scaffold, while partially coupled elsewhere to the peptide) were not observed on any occasion. The reaction with more constrained scaffolds (i.e. TOHPT(IAc3), see Table 1) was slower (~1 hour). Intermediate coupling products were not observed on this occasion either (i.e. +1 HI, +2 HI).

A Pep48-37 derivative, where all Cys were replaced by Lys, did not show appreciable modification by THME(IAc3) after 2 hours—indicating good selectivity of the iodoacetyl functionality for cysteines. The acrylated scaffolds THME (Acr3) and TPBA(Acr3) coupled to the 3-Cys peptides as well, albeit at a slower rate (~<1 hr).

TABLE 1

List of Scaffolds synthesised and tested against Peptides containing 3 Cysteines.

| Name | MW [a] | Scaffold Precursors [b] | Thiol-reactive Scaffold, final product [c] | Chemistry |
| --- | --- | --- | --- | --- |
| THME(IAc3) Trishydroxy-methylethane trisiodoacetate | 239 | (structure) | (structure) | Iodoacetyl |

TABLE 1-continued

List of Scaffolds synthesised and tested against Peptides containing 3 Cysteines.

| Name | MW [a] | Scaffold Precursors [b] | Thiol-reactive Scaffold, final product [c] | Chemistry |
|---|---|---|---|---|
| PE(IAc4) Pentaerythritol tetraiodoacetate | 296 | | | Iodoacetyl |
| TEA(IAc3) Triethanolamine trisiodoacetate | 272 | | | Iodoacetyl |
| TPEA(IAc3) (R,R,R)-tris(2-phenyl)-ethanolamine trisiodoacetate | 500 | | | Iodoacetyl |

TABLE 1-continued

List of Scaffolds synthesised and tested against Peptides containing 3 Cysteines.

| Name | MW [a] | Scaffold Precursors [b] | Thiol-reactive Scaffold, final product [c] | Chemistry |
|---|---|---|---|---|
| TPBA(IAc3) (Tris p-benzyl)amine trisiodoacetate Tris p-methyl-phenylamine trisiodoacetate | 455 | 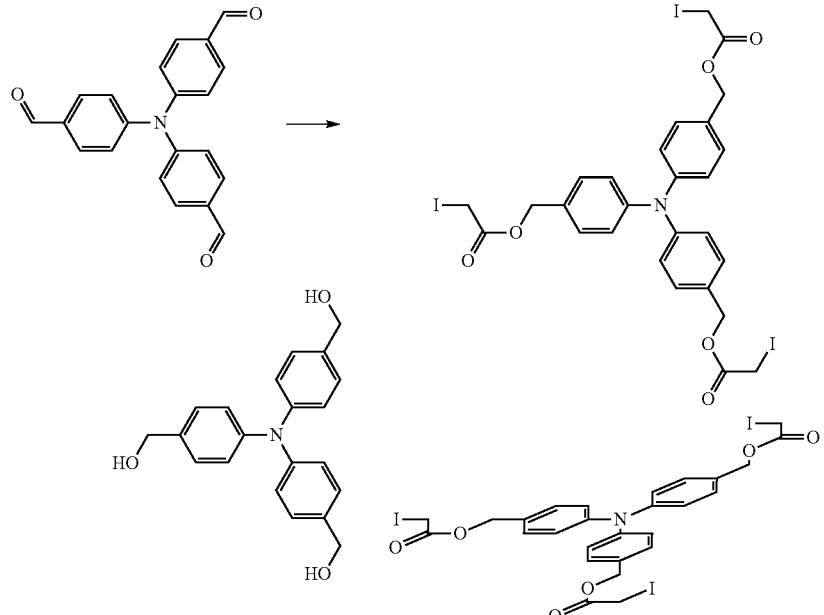 | 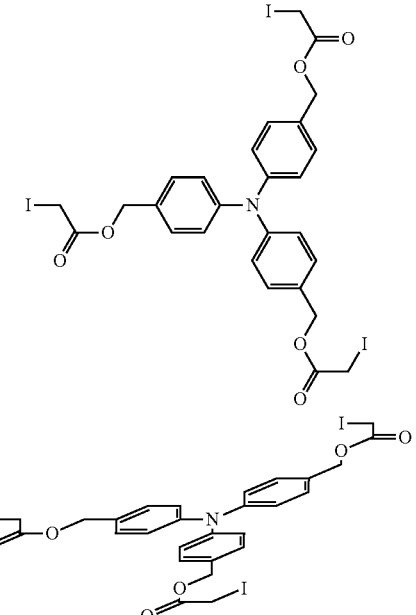side view | Iodoacetyl |
| TOHPT(IAc3) Tris o-hydroxyphenyl triazine trisiodoacetate | 477 | 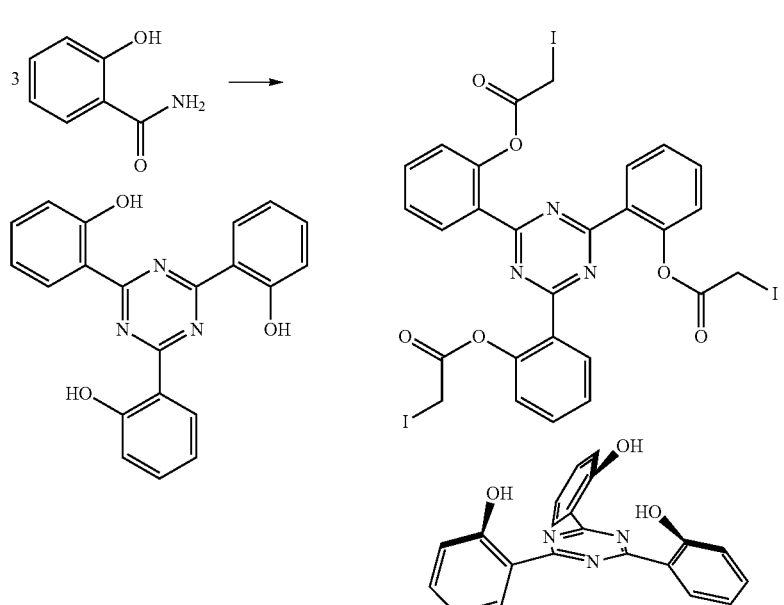 | 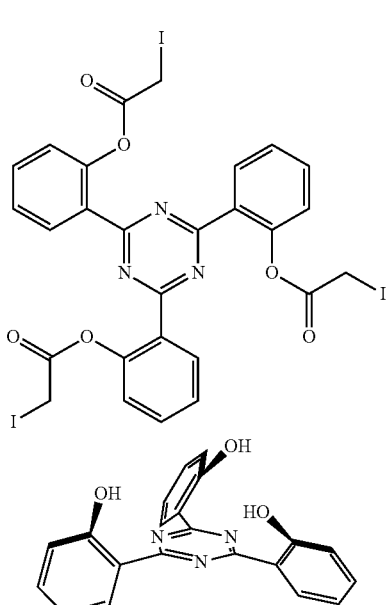3-D view | Iodoacetyl |

TABLE 1-continued

List of Scaffolds synthesised and tested against Peptides containing 3 Cysteines.

| Name | MW [a] | Scaffold Precursors [b] | Thiol-reactive Scaffold, final product [c] | Chemistry |
|---|---|---|---|---|
| THME(Acr3) Trishydroxy-methyl-ethane trisacrylate | 282[d] | *(structure: trishydroxymethylethane with three OH groups)* | *(structure: trishydroxymethylethane trisacrylate)* | Acryloyl |
| TPT(Acr3) Trispiperazine-triazine triacrylate | 496[d] | *(structure: cyanuric chloride + 3 Boc-piperazine → tris-Boc-piperazine-triazine)* | *(structure: trispiperazine-triazine triacrylate)* | Acryloyl |

[a] The molecule weight corresponds to the mass addition to a 3-Cys peptide assuming all 3 iodines and 3 hydrogens have been displaced for any of the iodoacetyl-containing scaffolds.
[b] Starting materials employed for the synthesis of the precursor scaffold (excluding the thiol-reactive functionality).
[c] Final scaffold showing the thiol-reactive chemistry employed. On occasion more than one view of the molecule is shown (TBH/TOHBT-IAc3).
[d] As the addition reaction of acryloyl groups with thiols incurs no loss in mass, the MW indicated represents that of the entire scaffold Example 5 Use of Trishydroxymethylethane Trisiodoacetate (THME(IAc3)) Cores As described in Example 1, peptide conjugates were made by selection against the protein MDM2. In the case of PEP48 the sequence of the second loop was randomized, and the phage repertoire subjected to further rounds of selection. This led to several conjugates with improved binding affinity (see Example 4 for sequences of several such PEP48 derivatives). One of these, the conjugate PEP48-3s1 had a binding affinity as measured by fluorescence anisotropy in the range 27 to 100 nM.

The same peptide PEP48-3s1 was conjugated as above with THME(IAc3) instead of TBMB, as described in Example 4. The three iodoacetyl groups are expected to react with up to three cysteine residues of a peptide; in this case the core is expected to impose a tetrahedral geometry on the peptide, and lead to two stereoisomers. This is consistent with the two peaks of identical mass seen on purification of the conjugate with HPLC, which had different binding affinities when measured by fluorescence anisotropy (640 nM and 1600 nM).

Thus as expected the different geometry and packing imposed by the THME(IAc3) core differs from that imposed by the TBMB core, and leads to an altered binding affinity.

Example 6 Making Core Variants: Synthetic Pathway to Benzoxazole Derivatives

By way of illustration, a reagent to make cores, such as TBMB, can be chemically derivatized to make variant cores. The following example indicates two synthetic pathways that might be used to create benzoxazole derivatives.

Scheme 1-Direct pathway

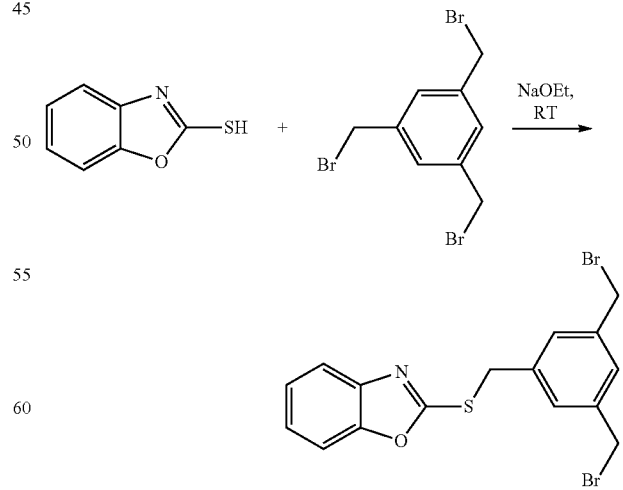

Koci et al, *Bioorg Med Chem Lett,* 2002, 12, 3275-3278.
2-mercaptobenzoxazole (5 mmol, 151 mg), dissolved in dry DMF (8 mL), is added to a solution of sodium (5 mmol, 115 mg) in dry ethanol (2.5 mL). After 10 min of stirring at room temperature, TBMB (5 mmol, 1.785 g) is added by portions and the resultant suspension is stirred for 6 hours. The reaction mixture is then poured into an ice bath and left overnight. The solid obtained is filtered off, washed with cold water (3×20 mL) and air-dried. The crude product is purified by flash chromatography using EtOAc-hexane (20/80) as eluent system.

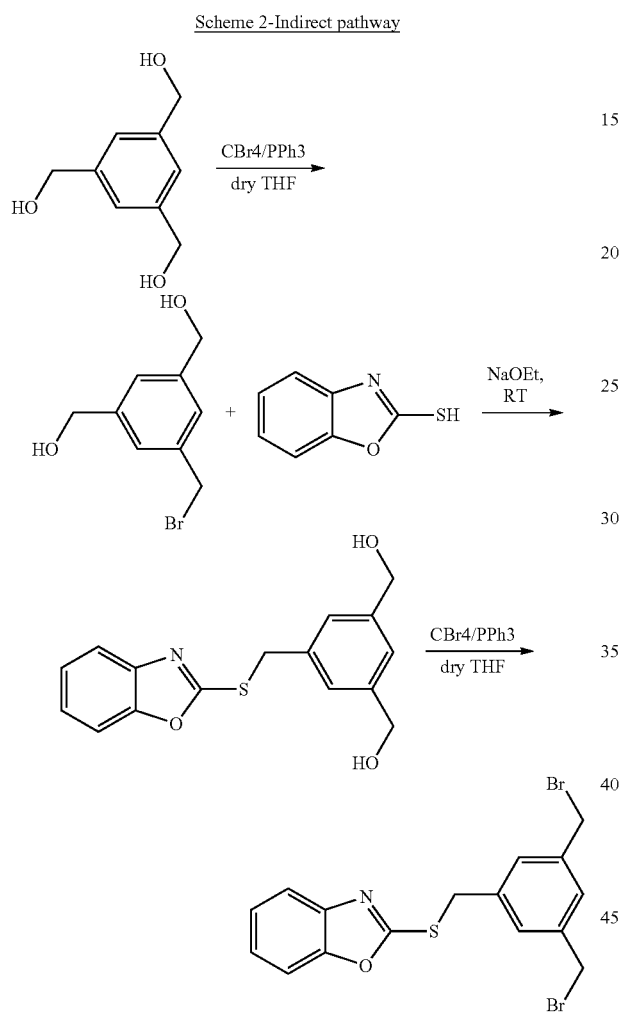

Heinen et al, *Angewandte Chemie*, 2000, 39, 806-809.

1,3,5-Tris(hydroxymethyl)benzene (11.9 mmol) and triphenylphosphine (11.9 mmol) are stirred under argon in 100 mL dry THF. The flask is cooled to 0° C. and tetrabromomethane (11.9 mmol) is added. The solution is stirred at room temperature for 2.5 h and the reaction is monitored through TLC. Triphenylphosphineoxide, which settled down, was filtered. The filtrate was evaporated to give a residue which was then fractionated by flash chromatography using EtOAc as eluent to obtain bromomethyl-3,5-bis(hydroxymethyl)benzene.

2-mercaptobenzoxazole (5 mmol), dissolved in dry DMF (8 mL), is added to a solution of sodium (5 mmol) in dry ethanol (2.5 mL). After 10 min of stirring at room temperature, bromomethyl-3,5-bis(hydroxymethyl)benzene (5 mmol) is added by portions and the resultant suspension is stirred for 6 hours. The reaction mixture is then poured into an ice bath and left overnight. The solid obtained is filtered off, washed with cold water (3×20 mL) and air-dried. The crude product is purified by flash chromatography using EtOAc-hexane (20/80) as eluent system.

Benzoxazolyl-2'-thiomethyl-3,5-bis(hydroxymethyl)benzene (1.2 mmol) and triphenylphosphine (1.2 mmol) are stirred under argon in 10 mL dry THF. The flask is cooled to 0° C. and tetrabromomethane (1.2 mmol) is added. The solution is stirred at room temperature for 2.5 h and the reaction is monitored through TLC. Triphenylphosphineoxide, which settled down, was filtered. The filtrate was evaporated to give a residue which was then fractionated by flash chromatography using EtOAc as eluent to obtain benzoxazolyl-2'-thiomethyl-3,5-bis(bromomethyl)benzene.

Such benzoxazole conjugates might be used according to the invention as follows. The polypeptides of a first repertoire of polypeptide ligands comprising two cysteine residues separated by a loop sequence conjugated to dibromomethylbenzene, could be conjugated to the above product of benzoxazole and TBMB. This is expected to alter the conformational diversity of the first repertoire as the second repertoire of polypeptides will comprise an extra benzoxazole ring attached to the scaffold. In turn this may provide ligands selected from the second repertoire with additional constraints and binding contacts (leading to improved affinity and/or specificity to target, and/or enhanced protease resistance).

The addition of other functions to the core for example moieties that bind to serum albumin (for half-life extension), or guanidine moieties (for cell penetration), or enzyme inhibitors, or toxic drugs (for cell killing) could also be used to alter the conformational diversity of a repertoire.

Example 7 Orthogonal Reactive Groups of the Scaffold

A peptide comprising the first loop of the kallikrein inhibitor PK15 (with additional aspartic acid residues at the N- and C-terminus) was coupled to TBMB and subsequently to propylargylamine to yield the product below:

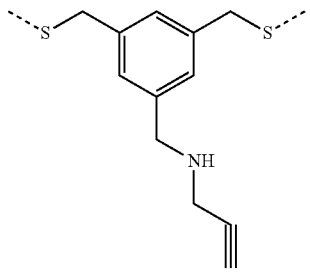

The reaction details are as follows: PK15-L1DD ((Ac)-DCSDRFRNCD-(NH$_2$) (SEQ ID No. 11)) (5 mg) in 600 µl water was treated with TCEP (60 µl) for 30 mins and then HPLC purified (2 runs, eluted in ca 7 ml buffer, m/z 1271). The buffer was treated with an equal volume of 100 mM ammonium bicarbonate to pH ~8 and TBMB (5 equivalents, 7 mg in 0.5 ml MeCN) and reaction left at room temperature. After 20 mins MALDI MS showed completion of reaction (m/z 1375) and the reaction quenched with propargylamine (50 equivalents, 10 µl) and the reaction left overnight. The product was HPLC purified and lyophilised to a white powder (m/z 1440, calc. 1440).

The propargylamine provides a scaffold reactive group that is orthogonal to the benzylic bromines of TBMB. It is capable of reacting by click chemistry with an azido function within or attached to the polypeptide, and thereby creating a second polypeptide loop. Azido functions can be provided by incorporation of azido amino acids (for example azido-tyrosine) into the polypeptide, or by using bifunctional linkers.

Furthermore the propargylamine is capable of reacting with other polypeptides; here we describe its use to couple to a second polypeptide ligand to make a bifunctional ligand.

Firstly a peptide comprising the first loop of the MDM2 inhibitor PEP48 (with additional aspartic acid residues at the N- and C-terminus) was coupled to DBMB follows. Pep48-L1DD ((H)-DGCVRFGWTCD-(NH$_2$)) (SEQ ID No. 12)) (5 mg) in 600 µl water was treated with TCEP (60 µl) for 30 mins and then HPLC purified (2 runs, eluted in ca 7 ml buffer, m/z 1258). The buffer was treated with an equal volume of 100 mM ammonium bicarbonate to pH ~8 and DBMB (5 mg in 0.5 ml MeCN) and reaction left at room temperature. After 20 mins MALDI MS showed completion of reaction and product purified by HPLC, and lyophilised. The product was re-dissolved in water (1 ml) and to this added 10 equivalents of the azide linker (see structure below, 4.5 mg in 100 µl 100 mM ammonium carbonate) and EDC (5 mg in 100 µl water) and reaction left overnight. MALDI MS showed desired product (m/z 1471, calc. 1472), which was purified by HPLC.

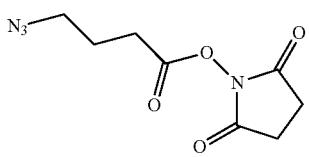 [SMILES: [N-]=[N+]=NCCCC(=O)ON1C(=O)CCC1=O]

The PK15-L1DD-TBMB-propargylamine conjugate (ca 1 mg, ca 0.7 µmole) was then dissolved in 0.5 ml water and to this added sodium ascorbate (50 µl of 25 µM in 200 mM NaCl), copper sulphate (25 µl of 2.5 µM in 200 mM NaCl) and the azide linker-modified Pep48-L1 DD-DBMB conjugate (above, ca 1 mg). MALDI MS showed product after 1 hr which was HPLC purified (m/z 2911, calc. 2910 for expected structure as below)

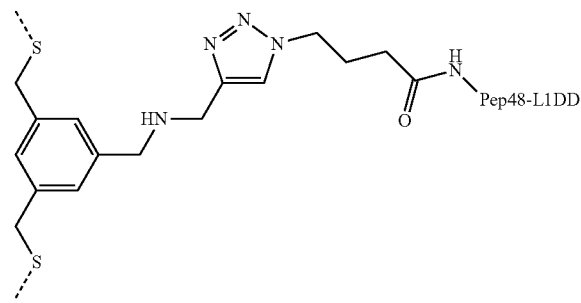

Example 8 Altering Reactive Groups of the Peptide

Earlier experiments had shown the reaction of cysteine with TBMB. Methionine was found to react with both TBMB and DBMB. A solution of methionine (1 mg/ml) in 1:1 acetonitrile:water and 25 mM ammonium bicarbonate was treated with either DBMB or TBMB (1 mg/ml in MeCN). Reaction was monitored by LC-MS after 1 hr reaction. With DBMB methionine showed a product m/z 334 (calc. 333 for single addition of DBMB) and with TBMB a product of m/z 426 (calc. for single addition of TBMB), see proposed product below:

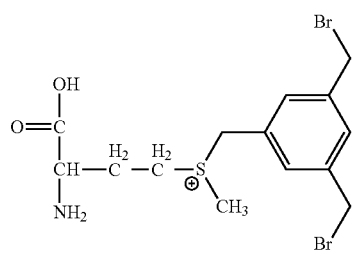 [SMILES: C[S+](CCC(N)C(=O)O)Cc1cc(CBr)cc(CBr)c1]

When we altered the central cysteine of the PK15 peptide to methionine [sequence (H)-ACSDRFRNMPADEALCG-(OH) (SEQ ID No. 13)] and reacted it with TBMB, we observed two peaks on HPLC with identical mass, with mass (1884) as expected to a conjugate of the TBMB through both cysteines and the single methionine. Both products inhibited the activity of kallikrein, but with IC50 values above 10 micromolar. Thus the changing of cysteine for methionine has a dramatic effect on the binding affinity presumably due to altered packing interactions from the additional methylene and methyl groups, and/or geometry of bonds around the methionine sulphur atom, and/or additional positive charge.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for altering the conformation of a first polypeptide ligand or group of polypeptide ligands, wherein each polypeptide ligand comprises at least three reactive groups each separated by a loop sequence and wherein the at least three reactive groups are linked to a molecular scaffold which forms covalent bonds with the at least three reactive groups, to produce a second polypeptide ligand or group of polypeptide ligands, comprising assembling the second ligand or group of ligands from the polypeptide(s) and molecular scaffold of the first ligand or group of ligands by altering at least one of the three reactive groups to cysteine, selenocysteine or methionine.

2. A method according to claim 1, comprising a further step of incorporating one of: (a) altering a nature of the molecular scaffold that forms covalent bonds with the at least three reactive groups; (b) altering a bond between at least one of the at least three reactive groups; or (c) any combination of (a) or (b).

3. A method according to claim 1, wherein the reactive groups are cysteine or methionine.

4. A method according to claim 2, wherein the further step comprises altering a nature of the molecular scaffold that forms covalent bonds with the at least three reactive groups and the altered molecular scaffold is asymmetric.

5. A method according to claim 4, wherein the molecular scaffold comprises three or more scaffold reactive groups which are capable of forming covalent bonds with the at least three reactive groups on the polypeptides, and wherein two or more reactive groups of the at least three reactive groups are not identical.

6. A method according to claim 5, wherein one of said scaffold reactive groups is orthogonal.

7. A method according to claim 1, wherein the scaffold reactive groups are selected from benzylic halides, α-halocarboxylic acids and acryloyl moieties.

8. A method according to claim 1, wherein at least one bond between the molecular scaffold and the polypeptide are chemically modified after assembly of the polypeptide and the molecular scaffold.

9. A method according to claim 8, wherein at least one thio-ether linkage between the polypeptide and the molecular scaffold is oxidised to form a sulphoxide or a sulphone.

10. A method according to claim 1, wherein the first group of polypeptide variants is a first repertoire of polypeptide variants.

11. A method according to claim 1, wherein the second group of polypeptide variants is a second repertoire of polypeptide variants.

* * * * *

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial sequence
<220> FEATURE:
<223> OTHER INFORMATION: Synthetic sequence: Encoded polypeptide library
<220> FEATURE:
<221> NAME/KEY: VARIANT
<222> LOCATION: (3)..(8)
<223> OTHER INFORMATION: Xaa stands for a random natural amino acid
<220> FEATURE:
```

```
<221> NAME/KEY: VARIANT
<222> LOCATION: (10)..(15)
<223> OTHER INFORMATION: Xaa stands for a random natural amino acid

<400> SEQUENCE: 1

Ala Cys Xaa Xaa Xaa Xaa Xaa Cys Xaa Xaa Xaa Xaa Xaa Cys
1               5                   10                  15

Gly

<210> SEQ ID NO 2
<211> LENGTH: 15
<212> TYPE: PRT
<213> ORGANISM: Artificial sequence
<220> FEATURE:
<223> OTHER INFORMATION: Synthetic sequence

<400> SEQUENCE: 2

Cys Phe Asn Ser Glu Trp Ser Cys Leu Gln Ser Cys Ser Asn Cys
1               5                   10                  15

<210> SEQ ID NO 3
<211> LENGTH: 220
<212> TYPE: PRT
<213> ORGANISM: fd phage

<400> SEQUENCE: 3

Ala Glu Thr Val Glu Ser Cys Leu Ala Lys Pro His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Gly Ser Gly Gly Gly Ser Glu Gly Gly
65                  70                  75                  80

Gly Ser Glu Gly Gly Gly Thr Lys Pro Pro Glu Tyr Gly Asp Thr Pro
                85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
        115                 120                 125

Gln Pro Leu Asn Thr Phe Met Phe Gln Asn Asn Arg Phe Arg Asn Arg
    130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

Gly Phe Asn Glu Asp Pro Phe Val Cys Glu Tyr Gln Gly Gln Ser Ser
        195                 200                 205

Asp Leu Pro Gln Pro Pro Val Asn Ala Pro Ser Gly
    210                 215                 220

<210> SEQ ID NO 4
<211> LENGTH: 220
<212> TYPE: PRT
<213> ORGANISM: Artificial sequence
```

```
<220> FEATURE:
<223> OTHER INFORMATION: Synthetic sequence: Domains D1 and D2 of clone
      21

<400> SEQUENCE: 4

Ala Glu Thr Val Glu Ser Ser Leu Ala Lys Ser His Ile Glu Gly Ser
1               5                   10                  15

Phe Thr Asn Val Trp Lys Asp Lys Thr Leu Asp Trp Tyr Ala Asn
            20                  25                  30

Tyr Glu Gly Ile Leu Trp Lys Ala Thr Gly Val Val Ile Thr Gly
        35                  40                  45

Asp Glu Thr Gln Val Tyr Ala Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Gly Thr Lys Pro Pro Glu Tyr Gly Asp Thr Pro
                85                  90                  95

Ile Pro Gly Tyr Ile Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
        115                 120                 125

His Pro Leu Asn Thr Phe Met Phe Gln Asn Asn Arg Phe Arg Asn Arg
    130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Val Ala Phe His Ser
            180                 185                 190

Gly Phe Asn Glu Asp Leu Leu Val Ala Glu Tyr Gln Gly Gln Ser Ser
        195                 200                 205

Tyr Leu Pro Gln Pro Pro Val Asn Ala Pro Ser Gly
    210                 215                 220

<210> SEQ ID NO 5
<211> LENGTH: 18
<212> TYPE: PRT
<213> ORGANISM: Artificial sequence
<220> FEATURE:
<223> OTHER INFORMATION: Synthetic sequence: PEP10

<400> SEQUENCE: 5

Ser Cys Glu Leu Trp Asn Pro Lys Cys Arg Leu Ser Pro Phe Glu Cys
1               5                   10                  15

Lys Gly

<210> SEQ ID NO 6
<211> LENGTH: 18
<212> TYPE: PRT
<213> ORGANISM: Artificial sequence
<220> FEATURE:
<223> OTHER INFORMATION: Synthetic sequence: PEP48

<400> SEQUENCE: 6

Ser Cys Val Arg Phe Gly Trp Thr Cys Asp Asn Ser Trp His Gly Cys
1               5                   10                  15

Lys Gly
```

```
<210> SEQ ID NO 7
<211> LENGTH: 12
<212> TYPE: PRT
<213> ORGANISM: Artificial sequence
<220> FEATURE:
<223> OTHER INFORMATION: Synthetic sequence: Peptide pMI

<400> SEQUENCE: 7

Thr Ser Phe Ala Glu Tyr Trp Asn Leu Leu Ser Pro
1               5                   10

<210> SEQ ID NO 8
<211> LENGTH: 17
<212> TYPE: PRT
<213> ORGANISM: Artificial sequence
<220> FEATURE:
<223> OTHER INFORMATION: Synthetic sequence: Pep48-3s1 of
      PCT/EP2010/004948

<400> SEQUENCE: 8

Ser Asp Asp Cys Val Arg Phe Gly Trp Thr Cys Pro Thr Val Met Cys
1               5                   10                  15

Gly

<210> SEQ ID NO 9
<211> LENGTH: 19
<212> TYPE: PRT
<213> ORGANISM: Artificial sequence
<220> FEATURE:
<223> OTHER INFORMATION: Synthetic sequence: Pep48-58 of
      PCT/EP2010/004948

<400> SEQUENCE: 9

Ser Asp Asp Cys Val Arg Phe Gly Trp Thr Cys Glu Pro Ser Leu Pro
1               5                   10                  15

Gly Cys Gly

<210> SEQ ID NO 10
<211> LENGTH: 18
<212> TYPE: PRT
<213> ORGANISM: Artificial sequence
<220> FEATURE:
<223> OTHER INFORMATION: Synthetic sequence: Pep48-37 of
      PCT/EP2010/004948

<400> SEQUENCE: 10

Ser Asp Cys Val Arg Phe Gly Trp Thr Cys Ser Pro Gly Met Val Gly
1               5                   10                  15

Cys Asp

<210> SEQ ID NO 11
<211> LENGTH: 10
<212> TYPE: PRT
<213> ORGANISM: Artificial sequence
<220> FEATURE:
<223> OTHER INFORMATION: Synthetic sequence: PK15-L1DD of
      PCT/EP2010/004948

<400> SEQUENCE: 11

Asp Cys Ser Asp Arg Phe Arg Asn Cys Asp
1               5                   10

<210> SEQ ID NO 12
<211> LENGTH: 11
<212> TYPE: PRT
<213> ORGANISM: Artificial sequence
```

```
<220> FEATURE:
<223> OTHER INFORMATION: Synthetic sequence: Pep48-L1DD of
      PCT/EP2010/004948

<400> SEQUENCE: 12

Asp Gly Cys Val Arg Phe Gly Trp Thr Cys Asp
1               5                   10

<210> SEQ ID NO 13
<211> LENGTH: 17
<212> TYPE: PRT
<213> ORGANISM: Artificial sequence
<220> FEATURE:
<223> OTHER INFORMATION: Synthetic sequence: PK15 peptide with central
      cysteine altered to methionine

<400> SEQUENCE: 13

Ala Cys Ser Asp Arg Phe Arg Asn Met Pro Ala Asp Glu Ala Leu Cys
1               5                   10                  15

Gly
```